United States Patent
Zilberman et al.

(10) Patent No.: US 8,483,820 B2
(45) Date of Patent: Jul. 9, 2013

(54) SYSTEM AND METHOD FOR PERCUTANEOUS DELIVERY OF ELECTRICAL STIMULATION TO A TARGET BODY TISSUE

(75) Inventors: Yitzhak Zilberman, Santa Clarita, CA (US); James M. McHargue, Grafton, WI (US); Arkady Glukhovsky, Santa Clarita, CA (US)

(73) Assignee: Bioness Inc., Valencia, CA (US)

( * ) Notice: Subject to any disclaimer, the term of this patent is extended or adjusted under 35 U.S.C. 154(b) by 1124 days.

(21) Appl. No.: 11/867,454

(22) Filed: Oct. 4, 2007

(65) Prior Publication Data

US 2008/0243216 A1    Oct. 2, 2008

Related U.S. Application Data

(60) Provisional application No. 60/828,376, filed on Oct. 5, 2006.

(51) Int. Cl.
*A61N 1/372* (2006.01)

(52) U.S. Cl.
USPC ...... 607/2; 607/37; 607/61; 607/75; 607/116; 607/149

(58) Field of Classification Search
None
See application file for complete search history.

(56) References Cited

U.S. PATENT DOCUMENTS

| 3,204,637 A | 9/1965 | Frank et al. |
|---|---|---|
| 3,426,748 A | 2/1969 | Bowers |
| 3,774,618 A | 11/1973 | Avery |
| 3,835,864 A | 9/1974 | Rasor et al. |
| 3,964,470 A | 6/1976 | Trombley |
| 3,995,644 A | 12/1976 | Parsons |
| 4,032,860 A | 6/1977 | LeVeen |
| 4,102,344 A | 7/1978 | Conway et al. |
| 4,323,999 A | 4/1982 | Yoshizawa et al. |
| 4,417,888 A | 11/1983 | Cosentino et al. |
| 4,419,995 A | 12/1983 | Hochmair et al. |
| 4,793,353 A | 12/1988 | Borkan |
| 4,987,897 A | 1/1991 | Funke |
| 5,080,099 A | 1/1992 | Way et al. |
| 5,098,397 A | 3/1992 | Svensson et al. |

(Continued)

FOREIGN PATENT DOCUMENTS

| JP | 61-122870 A | 6/1986 |
|---|---|---|
| JP | 62-286471 | 12/1987 |

(Continued)

OTHER PUBLICATIONS

International Search Report and Written Opinion for Application No. PCT/US2007/080564, completed Apr. 8, 2008.

(Continued)

*Primary Examiner* — Kennedy Schaetzle
(74) *Attorney, Agent, or Firm* — Cooley LLP

(57) ABSTRACT

An apparatus includes a percutaneous connection port configured to convey an electrical signal between an electrical device disposed outside of a body and an electrical member disposed within the body. The percutaneous connection port has a distal portion and a proximal portion. The proximal portion includes a surface configured to be accessible from a region of the body. The distal portion includes an anchor configured to be disposed within the body. The anchor has a curved shape about an axis substantially parallel to a skin of the body.

15 Claims, 9 Drawing Sheets

U.S. PATENT DOCUMENTS

| | | | |
|---|---|---|---|
| 5,325,870 | A | 7/1994 | Kroll et al. |
| 5,330,516 | A | 7/1994 | Nathan |
| 5,356,428 | A | 10/1994 | Way |
| 5,441,518 | A | 8/1995 | Adams et al. |
| 5,441,527 | A | 8/1995 | Erickson et al. |
| 5,443,065 | A | 8/1995 | Berghoff et al. |
| 5,465,715 | A | 11/1995 | Lyons |
| RE35,129 | E | 12/1995 | Pethica et al. |
| 5,531,782 | A | 7/1996 | Kroll et al. |
| 5,545,191 | A | 8/1996 | Mann et al. |
| 5,562,707 | A | 10/1996 | Prochazka et al. |
| 5,674,253 | A | 10/1997 | Adams et al. |
| 5,766,231 | A | 6/1998 | Erickson et al. |
| 5,782,645 | A | 7/1998 | Stobie et al. |
| 5,796,827 | A | 8/1998 | Coppersmith et al. |
| 5,807,397 | A | 9/1998 | Barreras |
| 5,843,132 | A | 12/1998 | Ilvento |
| 5,914,701 | A | 6/1999 | Gersheneld et al. |
| 5,916,244 | A | 6/1999 | Walters |
| 6,006,122 | A | 12/1999 | Smits et al. |
| 6,070,103 | A * | 5/2000 | Ogden ............................ 607/60 |
| 6,073,050 | A | 6/2000 | Griffith |
| 6,076,016 | A | 6/2000 | Feierbach |
| 6,214,032 | B1 | 4/2001 | Loeb et al. |
| 6,233,488 | B1 * | 5/2001 | Hess ............................... 607/58 |
| 6,266,567 | B1 | 7/2001 | Ishikawa et al. |
| 6,282,448 | B1 | 8/2001 | Katz et al. |
| 6,366,814 | B1 | 4/2002 | Boveja et al. |
| 6,393,323 | B1 | 5/2002 | Sawan |
| 6,415,184 | B1 | 7/2002 | Ishikawa et al. |
| 6,438,428 | B1 | 8/2002 | Axelgaard et al. |
| 6,505,082 | B1 | 1/2003 | Scheiner et al. |
| 6,564,102 | B1 | 5/2003 | Boveja |
| 6,607,500 | B2 | 8/2003 | Da Silva et al. |
| 6,629,968 | B1 | 10/2003 | Jain et al. |
| 6,635,045 | B2 | 10/2003 | Keusch et al. |
| 6,668,191 | B1 | 12/2003 | Boveja |
| 6,725,096 | B2 * | 4/2004 | Chinn et al. .................. 607/115 |
| 6,735,474 | B1 | 5/2004 | Loeb et al. |
| 6,735,475 | B1 | 5/2004 | Whitehurst et al. |
| 6,754,472 | B1 | 6/2004 | Williams et al. |
| 6,829,508 | B2 | 12/2004 | Schulman et al. |
| 6,829,510 | B2 | 12/2004 | Nathan et al. |
| 6,840,919 | B1 | 1/2005 | Håkansson |
| 6,847,844 | B2 | 1/2005 | Sun et al. |
| 6,892,098 | B2 | 5/2005 | Ayal et al. |
| 6,896,675 | B2 | 5/2005 | Leung et al. |
| 6,928,320 | B2 | 8/2005 | King |
| 6,941,171 | B2 | 9/2005 | Mann et al. |
| 7,004,948 | B1 * | 2/2006 | Pianca et al. .................. 606/129 |
| 7,013,179 | B2 | 3/2006 | Carter et al. |
| 7,324,853 | B2 | 1/2008 | Ayal et al. |
| 7,389,145 | B2 | 6/2008 | Kilgore et al. |
| 7,415,309 | B2 * | 8/2008 | McIntyre ....................... 607/116 |
| 7,502,652 | B2 | 3/2009 | Gaunt et al. |
| 7,536,226 | B2 | 5/2009 | Williams et al. |
| 2001/0002441 | A1 | 5/2001 | Boveja |
| 2002/0055779 | A1 | 5/2002 | Andrews |
| 2002/0111663 | A1 | 8/2002 | Dahl et al. |
| 2002/0193844 | A1 | 12/2002 | Michelson et al. |
| 2003/0171792 | A1 | 9/2003 | Zarinetchi et al. |
| 2003/0199807 | A1 | 10/2003 | Dent et al. |
| 2003/0212395 | A1 | 11/2003 | Woloszko et al. |
| 2003/0236557 | A1 | 12/2003 | Whitehurst et al. |
| 2004/0049235 | A1 | 3/2004 | Deno et al. |
| 2004/0130455 | A1 | 7/2004 | Prochazka |
| 2004/0176804 | A1 | 9/2004 | Palti |
| 2004/0199222 | A1 | 10/2004 | Sun et al. |
| 2004/0204686 | A1 | 10/2004 | Porter et al. |
| 2005/0070970 | A1 | 3/2005 | Knudson et al. |
| 2005/0136385 | A1 | 6/2005 | Mann et al. |
| 2005/0165461 | A1 | 7/2005 | Takeda et al. |
| 2005/0277841 | A1 | 12/2005 | Shennib |
| 2006/0184211 | A1 * | 8/2006 | Gaunt et al. ..................... 607/48 |
| 2006/0271118 | A1 | 11/2006 | Libbus et al. |
| 2007/0060975 | A1 | 3/2007 | Mannheimer et al. |
| 2007/0088419 | A1 | 4/2007 | Fiorina et al. |
| 2007/0265146 | A1 | 11/2007 | Kowalczewski et al. |
| 2008/0004676 | A1 | 1/2008 | Osypka et al. |
| 2009/0054952 | A1 | 2/2009 | Glukhovsky et al. |
| 2009/0177131 | A1 | 7/2009 | Dar et al. |
| 2009/0222053 | A1 | 9/2009 | Gaunt |
| 2009/0326602 | A1 | 12/2009 | Glukhovsky et al. |
| 2010/0016929 | A1 | 1/2010 | Prochazka |
| 2010/0076533 | A1 | 3/2010 | Dar et al. |
| 2010/0198298 | A1 | 8/2010 | Glukhovsky et al. |

FOREIGN PATENT DOCUMENTS

| | | |
|---|---|---|
| JP | 1-164373 A | 6/1989 |
| JP | 07-308392 | 11/1995 |
| JP | 10-509901 | 9/1998 |
| JP | 2003-501207 | 1/2003 |
| JP | 2007-531562 T | 11/2007 |
| WO | WO 94/29932 | 12/1994 |
| WO | WO 95/10323 | 4/1995 |
| WO | WO 00/57950 | 10/2000 |
| WO | WO 02/02182 | 1/2002 |
| WO | WO 02/38083 A1 | 5/2002 |
| WO | WO 2004/052450 | 6/2004 |
| WO | WO 2005/011541 A1 | 2/2005 |
| WO | WO 2005/037367 | 4/2005 |
| WO | WO 2005/070494 | 8/2005 |
| WO | WO 2006/101917 A2 | 9/2006 |
| WO | WO 2006/113654 A1 | 10/2006 |
| WO | WO 2007/002741 A1 | 1/2007 |
| WO | WO 2007/008906 A1 | 1/2007 |
| WO | WO 2007/082382 | 7/2007 |
| WO | WO 2008/140242 A1 | 11/2008 |
| WO | WO 2009/058258 A1 | 5/2009 |

OTHER PUBLICATIONS

Supplemental European Search Report for EP 07843903.1, mailed, Nov. 23, 2009.

International Search Report and Written Opinion for PCT/CA2010/001487, mailed Jan. 10, 2011.

Stoykov et al. "Recording Intramuscular EMG Signals Using Surface Electrodes," *2005 IEEE 9th International Conference on Rehabilitation Robotics*, Jun. 28-Jul. 1, 2005, Chicago, IL, pp. 291-294.

Prochazka et al "Clinical experience with reinforced, anchored intramuscular electrodes for functional neuromuscular stimulation," *Journal of Neuroscience Methods*, vol. 42 (1992), pp. 175-184.

Peckham et al. "Restoration of key grip and release in the C6 tetraplegic patient through functional electrical stimulation," *The Journal of Hand Surgery*, Sep. 1980, vol. 5, No. 5, St. Louis, MO, pp. 462-469.

Melzack et al. "Pain Mechanisms: A New Theory," *Science*, Nov. 19, 1965, vol. 150, No. 3699, pp. 971-979.

Tagusari et al. "Fine Trabecularized Carbon: Ideal Material and Texture for Percutaneous Device System of Permanent Left Ventricular Assist Device," *Artificial Organs*, Jun. 1998, vol. 22, No. 6, pp. 481-487.

Marsolais et al. "Implantation techniques and experience with percutaneous intramuscular electrodes in the lower extremities," *Journal of Rehabilitation Research and Development*, Veterans Administration, vol. 3, No. 3, pp. 1-8, Jul. 1986.

Masini et al. "Activated Pyrolytic Carbon Tip Pacing Leads: An Alternative to Steriod-Eluting Pacing Leads?" *Pacing and Clinical Electrophysiology*, Nov. 1996, vol. 19, No. 11, pp. 1663-2033.

"Innovative Medical Devices for Neuro-Technologies," *NeuroTECH*, [online] [Retrieved from the Internet on Sep. 21, 2007], Retrieved from the Internet URL [http://www.neurotech.be/Prod_cuffelectrode.htm].

Gans et al. "The Stimulus router: A Novel Means of Directing Current From Surface Electrodes to Nerves," *10th Annual Conference of the International FES Society*, Jul. 2005, Montreal, Canada, pp. 21-23.

Gans et al. "The Stimulus router: A Novel Means of Directing Current From Surface Electrodes to Nerves," *10th Annual Conference of the International FES Society*, Jul. 2005, Montreal, Canada, Display Poster.

Examination Report for Australian Patent Application No. AU 2007303034, mailed Oct. 28, 2010.

Examination Report for Australian Patent Application No. AU 2007303034, dated Sep. 23, 2011.

Abel-Gawad, M. et. al., "Reduction of bladder outlet resistance by selective stimulation of the ventral sacral root using high frequency blockage: a chronic study in spinal cord transected dogs," Journal of Urology, vol. 166 (2001), pp. 728-733.

Apkarian, J.A. et al., "Stretch reflex inhibition using electrical stimulation in normal subjects and subjects with spasticity," Journal of Biomedical Engineering, vol. 13 (1991), pp. 67-73.

Ashkan, K. et al., "Deep brain stimulation of the subthalamic nucleus in Parkinson's disease 1993-2003: where are we 10 years on?," Br J. Neurosurg, vol. 18 (2004), pp. 19-34.

Benabid, A.L. et al., "Combined (Thalamotomy and stimulation) stereotactic surgery of the VIM thalamic nucleus for bilateral Parkinson disease," Applied Neurophysiology, vol. 50 (1987), pp. 344-346.

Bhadra, N. et al., "High-frequency electrical conduction block of mammalian peripheral motor nerve," Muscle & Nerve (Epub ahead of Dec. 2005 print) (2005), pp. 782-790.

Brindley, G.S. et al., "Sacral anterior root stimulators for bladder control in paraplegia," Paraplegia, vol. 20 (1982), pp. 365-381.

Broseta, J. et al., "High-frequency cervical spinal cord stimulation in spasticity and motor disorders," Acta Neurochir Suppl (Wien), vol. 39 (1987), pp. 106-111.

Filali, M. et al., "Stimulation-induced inhibition of neuronal firing in human subthalamic nucleus," Exp Brain Res, vol. 156(3) (2004), pp. 274-281.

Glenn, W.W. et al., "Radiofrequency-controlled catheter pacemaker, Clinical application," New England Journal of Medicine, vol. 275 (1966), pp. 137-140.

Grill, W.M., Jr. et al., "Quantification of recruitment properties of multiple contact cuff electrodes," IEEE Trans. Rehabil. Eng., vol. 4(2) (1996), pp. 49-62.

Groen, J. et al., "Neuromodulation techniques in the treatment of the overactive bladder," BJU Int, vol. 87(8) (2001), pp. 723-731.

Handa, Y. et al., "Application of functional electrical stimulation to the paralyzed extremities," Neurologia Medico-Chirurgica, vol. 38 (1998), pp. 784-788.

Haugland, M., et al. Interfacing the body's own sensing receptors into neural prosthesis devices. Technology * Health Care, vol. 7 (1999), pp. 393-399.

Kilgore, K.L., et al. Chapter 6.2: Upper and lower extremity motor neuroprostheses. In Horch, K.W. And Dhillon, G.S., ed. Neuroprosthetics. Theory and Practice, vol. 2 World Scientific, New Jersey (2004), pp. 844-877.

Kilgore, K.L., et al. Block of Nerve Conduction Using High Frequency Alternating Current. $9^{th}$ Annual Conference of the International FES Society, Sep. 2004—Bournemouth, UK (2004).

Kralj, A.R. et al., "Functional Electrical Stimulation: Standing and Walking after Spinal Cord Injury," CRC Press, Boca Raton, FL (1989), pp. 1-15.

Landau, B. et al., "Neuromodulation techniques for medically refractory chronic pain," Annu Rev Med vol. 44 (1993), pp. 279-287.

Peckham, P.H. et al., "Implantable Neuroprosthesis Research G Efficacy of an implanted neuroprosthesis for restoring hand grasp in tetraplegia: a multicenter study," Archives of Physical Medicine & Rehabilitation vol. 82 (2001), pp. 1380-1388.

Prochazka, A. et al., "The Bionic glove: an electrical stimulator garment that provides controlled grasp and hand opening in quadriplegia," Arch. Phys. Med. Rehabil. vol. 78 (1997), pp. 608-614.

Shaker, H. et al., "Sacral root neuromodulation in the Treatment of Various Voiding and Storage Problems," International Urogynecology Journal vol. 10 (1999), pp. 336-343.

Shaker, H.S. et al., "Reduction of bladder outlet resistance by selective sacral root stimulation using high-frequency blockade in dogs: an acute study," J Urol 160 (3 Pt 1) (1997), pp. 901-907.

Solomonow, M. et al., "Control of muscle contractile force through indirect high-frequency stimulation," Am J Phys Med, vol. 62 (1983), pp. 71-82.

Strojnik, P. et al., "Treatment of drop foot using an implantable peroneal underknee stimulator," Scandanavian J. Of Rehabil. Med., vol. 19 (1987), pp. 37-43.

Tai, C. et al., "Block of external urethral sphincter contradiction by high frequency electrical stimulation of pudendal nerve," J Urol, vol. 172 (5 Pt 1) (2004), pp. 2069-2072.

Tai, C. et al., "Response of external urethral sphincter to high frequency biphasic electrical stimulation of pudendal nerve," J Urol, vol. 174(2) (2005), pp. 782-786.

Heeckeren, D.W. et al., "Electrophrenic respiration by radiofrequency induction," Journal of Thoracic & Cardiovascular Surgery, vol. 52 (1966), pp. 655-665.

Vodovnik, L., "Therapeutic effects of functional electrical stimulation of extremities," Medical and Biological Engineering & Computing, vol. 19 (1981), pp. 470-478.

Walker, J. et al., "Fundamentals of Physics," New Jersey, Hoboken, (2007), pp. 791-817.

Waltz, J.M., "Spinal cord stimulation: a quarter century of development and investigation. A review of its development and effectiveness in 1,336 cases," Stereotactic & Functional Neurosurgery, vol. 69 (1997), pp. 288-299.

Yu, D.T. et al., "Percutaneous intramuscular neuromuscular electric stimulation for the treatment of shoulder subluxation and pain in patients with chronic hemiplegia: a pilot study," Arch Phys Med Rehabil, vol. 82 (1997), pp. 20-25.

Office Action for Japanese Patent Application No. 2009-531624, mailed on Sep. 5, 2012.

* cited by examiner

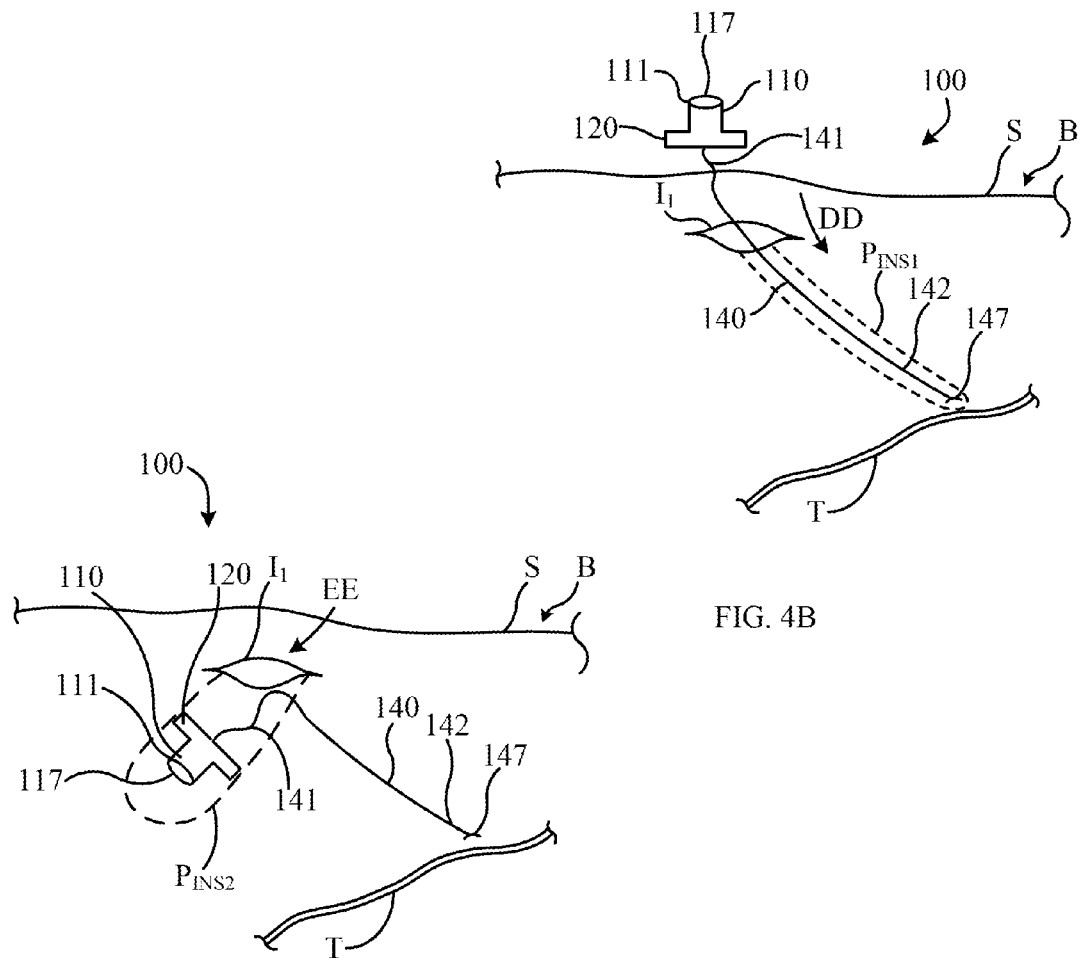
FIG. 4B
FIG. 4C
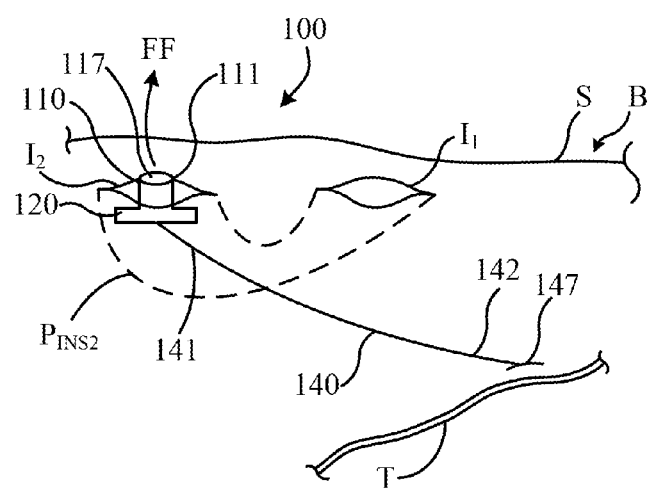
FIG. 4D

SYSTEM AND METHOD FOR PERCUTANEOUS DELIVERY OF ELECTRICAL STIMULATION TO A TARGET BODY TISSUE

CROSS-REFERENCE TO RELATED APPLICATIONS

This application claims priority to U.S. Provisional Application Ser. No. 60/828,376, entitled "System and Method for Percutaneous Delivery of Electrical Stimulation to a Target Body Tissue," filed Oct. 5, 2006, which is incorporated herein by reference in its entirety.

BACKGROUND

The invention relates generally to medical devices and procedures, and more particularly to systems and methods using a percutaneous connecting port to convey an electrical current between an electrical member disposed outside of a body and an electrical member disposed within the body.

Systems for conveying electrical current between an electrical member disposed outside of a body and targeted bodily tissue and/or an electrical member disposed within the body can be used in a variety of medical and/or therapeutic procedures. For example, some known procedures, such as transcutaneous electrical nerve stimulation (TENS), can include transmitting an electrical current to a targeted bodily tissue (e.g., a nerve, a muscle, or the like). Other known procedures can include transmitting an electrical current from a device (e.g., a sensor) implanted within the body to a device (e.g., a signal processor) disposed outside of the body. Other known procedures can include sensing and processing a biological electrical signal (e.g., an EMG signal) from within the body and transmitting the signal to an electrical device disposed outside of the body.

Some known systems for conveying electrical current between an electrical member disposed outside of a body and a targeted bodily tissue include one or more surface electrodes disposed on the skin of the body. Because the surface electrodes in such known systems do not penetrate the epidermis, the electrical current delivered by such known systems can be attenuated due to the electrical impedance of the skin. Accordingly, such known systems can require a high voltage and/or high current electrical source to deliver a therapeutically useful magnitude of electrical current to the targeted bodily tissue. Additionally, the electrical current passing through the skin can activate cutaneous receptors, resulting in patient discomfort (e.g., unpleasant sensations).

Some known systems for conveying electrical current between an electrical member disposed outside of a body and a targeted bodily tissue include an electrical connector having a portion disposed beneath the epidermis. Such known electrical connectors, however, can be difficult to implant and can easily become dislodged after implantation. Moreover, the pathway defined within the body for the implantation of such known electrical connectors can be a source for infection and/or discomfort.

Thus, a need exists for improved systems and methods for conveying an electrical current between an electrical member disposed outside of a body and a targeted bodily tissue and/or an electrical member disposed within the body.

SUMMARY

Systems and methods for conveying an electrical signal between an electrical member disposed outside of a body and targeted bodily tissue are described herein. In some embodiments, an apparatus includes a percutaneous connection port configured to convey an electrical signal between an electrical device disposed outside of a body and an electrical member disposed within the body. The percutaneous connection port has a distal portion and a proximal portion. The proximal portion includes a surface configured to be accessible from a region outside of the body. The distal portion includes an anchor configured to be disposed within the body. The anchor has a curved shape about an axis substantially parallel to the skin of the body.

BRIEF DESCRIPTION OF THE DRAWINGS

FIGS. 4B-4D are schematic illustrations showing a method of inserting the stimulation system shown in FIG. 1 into the body.

DETAILED DESCRIPTION

Figure 1:
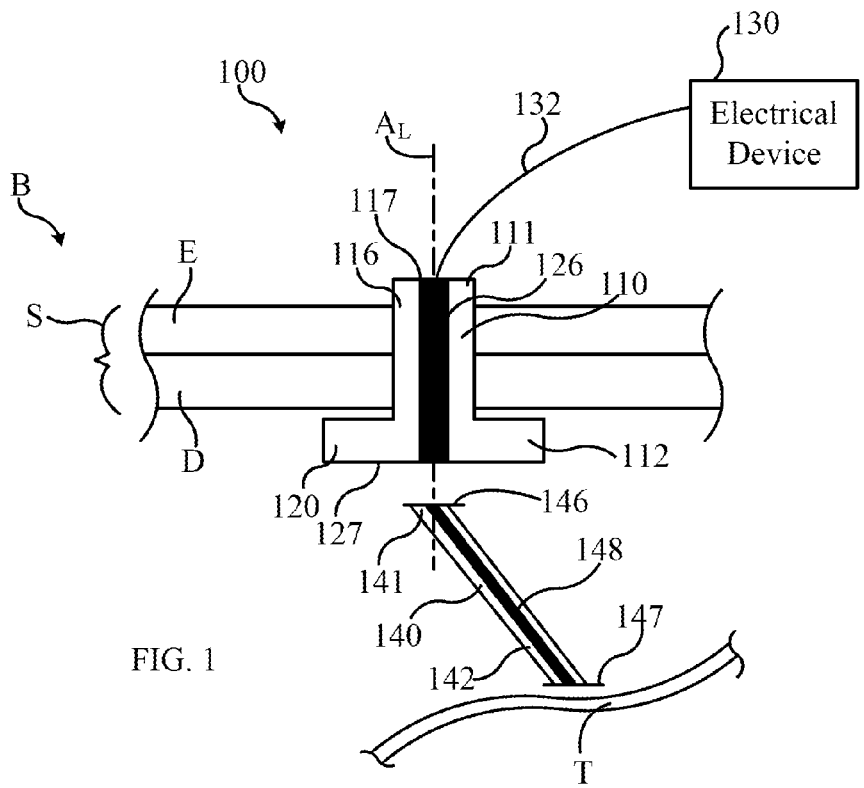
FIG. 1 is a schematic illustration of a stimulation system according to an embodiment of the invention disposed within a body.

In some embodiments, an apparatus includes a percutaneous connection port configured to convey an electrical signal between an electrical device disposed outside of a body and an electrical member disposed within the body and/or a bodily tissue. The electrical device disposed outside of the body can be, for example, a stimulator, a signal-processor, or the like. The electrical member disposed within the body can be, for example, an implanted device, a passive electrical conductor, or the like. The percutaneous connection port has a distal portion and a proximal portion. The proximal portion includes a surface configured to be accessible from a region outside of the body. In some embodiments, for example, the surface of the proximal portion can be flush with or above an outer surface of the body. The distal portion includes an anchor configured to be disposed within the body. The anchor has a curved shape about an axis substantially parallel to a skin of the body.

In some embodiments, a system includes an electrical device configured to be disposed outside of a body, an electrical member configured to be disposed entirely within the body, and a connection port. The electrical device, which can be, for example, a stimulator, a signal processor or the like, is configured to at least produce or receive an electrical signal (e.g., a current, a voltage or the like). The electrical member, which can be, for example, a passive electrical conductor, has a proximal end portion and a distal end portion. The connection port is configured to convey the electrical signal between the electrical device and the electrical member. The connection port is configured to be percutaneously inserted into the body such that a proximal portion of the connection port is disposed outside of the body and a distal portion of the connection port is disposed within the body. The proximal portion of the connection port is configured to be operatively coupled to the electrical device. The distal portion of the connection port is configured to be operatively coupled to and spaced apart from the electrical member.

In some embodiments, a method includes inserting an electrical member along a first path within a body such that a distal end portion of the electrical member is disposed at a target location within the body and a proximal end portion of the electrical member is disposed beneath a skin of the body. A connection port is inserted along a second path within the body such that a proximal portion of the connection port is accessible from a region outside of the body. In some embodiments, the connection port is inserted such that a distal portion of the connection port is spaced apart from and operatively coupled to the proximal end portion of the electrical member. In some embodiments, the second path can be different from the first path.

In some embodiments, a method includes operatively coupling an electrical device disposed outside of a body to a first connection port from a plurality of connection ports and a second connection port from the plurality of connection ports to define a first stimulation path within the body between the first connection port and the second connection port. A first electrical signal is conveyed from the electrical device into the body via at least one of the first connection port or the second connection port such that a portion of the first electrical signal travels within the body along the first stimulation path. The electrical device is operatively coupled to a third connection port from the plurality of connection ports to define a second stimulation path within the body, the second stimulation path being different than the first stimulation path. A second electrical signal is conveyed from the electrical device into the body via at least one of the first connection port, the second connection port or the third connection port such that a portion of the second electrical signal travels within the body along the second stimulation path.

In some embodiments, a method includes inserting a connection port within a body such that a distal portion of the connection port is disposed subcutaneously within the body and is spaced apart from a first electrical device disposed within the body, and a proximal portion of the connection port is accessible from a region outside of the body. An electrical signal is then conveyed from a second electrical device disposed outside of the body to the first electrical device disposed within the body via the connection port.

This application claims priority to U.S. Provisional Application Ser. No. 60/828,376, entitled "System and Method for Percutaneous Delivery of Electrical Stimulation to a Target Body Tissue," filed Oct. 5, 2006, which is incorporated herein by reference in its entirety. However, to the extent that a term is used and/or defined within this specification in a manner inconsistent with the use and/or definition provided in U.S. Provisional Application Ser. No. 60/828,376, the use and/or definition of the term shall be construed as provided within this specification.

As used in this specification, the words "proximal" and "distal" can refer to the direction closer to and away from, respectively, an operator (e.g., surgeon, physician, nurse, technician, etc.) who would use a medical device or a therapeutic device during a procedure. For example, the end of a medical device first to contact the patient's body would be the distal end, while the opposite end of the medical device (e.g., the end of the medical device being operated by the operator) would be the proximal end of the medical device. Similarly, the end of a medical device implanted the furthest within the patient's body would be the distal end, while the opposite end of the medical device (e.g., the end of the medical device that is implanted the least amount within the body or the end of the medical device that is disposed outside of the body) would be the proximal end.

As used in this specification the word "electrical member" refers to any object or device that can be used as a part of an electrical circuit or an electrical process. For example, in some embodiments, an electrical member can include passive objects, such as conductive wires, passive switches, insulators, electrical connectors or the like. In other embodiments, an electrical member can include an electrical device that produces, processes, receives and/or otherwise manipulates an electrical signal. Such electrical devices can include, for example, signal processors, sensors, stimulators, or the like.

FIG. 1 is a schematic illustration of a stimulation system 100 according to an embodiment of the invention disposed within a body B. The stimulation system 100 includes an electrical device 130 disposed outside of the body B, an electrical member 140 disposed within the body B, and a connection port 110 operatively coupled to the electrical device 130 and the electrical member 140. The connection port 110 includes a stud 116 and an anchor 120, and has a proximal portion 111 and a distal portion 112. The proximal portion 111 includes a connection surface 117. The distal portion 112 includes a terminal surface 127. The stud 116 defines a longitudinal axis $A_L$ and has an electrically conductive pathway 126 between the connection surface 117 and the terminal surface 127. In some embodiments, for example, the conductive pathway 126 can include the entire stud 116. In this manner, as described in more detail herein, an electrical signal, such as a current or a voltage, can be conveyed between an area outside of the body B and a target tissue T within the body B via an electrical pathway that excludes the skin S.

The stud 116 extends from the distal portion 112 of the connection port 110 through the skin S (including the dermis D and epidermis E) such that the longitudinal axis $A_L$ of the stud is non-parallel with a plane that includes an outer surface of the skin S. Moreover, the stud 116 extends through the skin S such that the connection surface 117 is flush with or above an outer surface of the skin S. Said another way, connection port 110 is disposed within the body B such that the connection surface 117 is accessible from an area outside of the body B. For example, in some embodiments, the connection surface 117 is disposed above the skin by between 0.5 mm and 5 mm. In this manner, as discussed in more detail herein, a connection wire 132 can be electrically coupled to the connection surface 117 of the connection port 110. Moreover, this arrangement can prevent the proximal end portion 111 of the connection port 110 from becoming caught on an object external to the body B (e.g., the patient's clothing) and is aesthetically pleasing.

The anchor 120 is disposed at the distal portion 112 of the connection port 110 beneath the skin S of the body B. The anchor 120 extends radially from the longitudinal axis $A_L$ of the stud 116 to anchor the connection port 110 in a subcutaneous location within the body B. Said another way, the anchor 120 is substantially circular about the longitudinal axis $A_L$ of the stud 116. In this manner, when the connection port 110 is percutaneously disposed within the body B, the anchor 120 maintains a location of the connection port 110 within the body B. Moreover, as discussed in more detail herein, in some embodiments, the anchor 120 can be configured to resist the extrusion and/or expulsion of the connection port 110 from the body B.

The electrical device 130 is operatively coupled to the connection port 110 by the connection wire 132. The connection wire 132 can be coupled to the connection port 110 by any suitable means, such as for example, by an adhesive, a snap connector, an alligator clip, a screw connector, a weld, a solder or the like. Although shown as being operatively coupled via a single connection wire 132, in other embodiments, the electrical device 130 can be operatively coupled to the connection port 110 using multiple connection wires to establish, for example, a bi-polar electrical connection. In such embodiments, the connection port 110 can include multiple distinct conductive pathways 126. In yet other embodiments, the electrical device 130 can be operatively coupled to the connection port 110 without any physical coupling or connection wire 132. For example, in some embodiments, the electrical device 130 can be operatively coupled to the connection port 110 via a galvanic coupling, a capacitive coupling, an inductive coupling, a radio frequency (RF) coupling and/or any suitable wireless coupling.

The electrical device 130 can be any suitable device configured to produce and/or receive an electrical signal, such as an electrical current, a voltage or the like. For example, in some embodiments, the electrical device 130 can be an electrical stimulator to produce an electrical current and/or voltage to stimulate a target tissue T, such as a nerve, a muscle and/or the like, within the body B as a part of a therapeutic process. In other embodiments, the electrical device 130 can be a signal processor configured to receive and/or process an electrical signal produced by the target tissue T and/or an electrical device (not shown in FIG. 1) disposed within the body B.

The electrical member 140 has a proximal end portion 141 and a distal end portion 142, and defines an electrically conductive path 148 therethrough. The proximal end portion 141 of the electrical member 140 includes a terminal 146 that is spaced apart from and operatively coupled to the distal end 112 of the connection port 110. In this manner, an electrical signal can be conveyed between the electrical device 130 and the electrical member 140 via the connection port 110. Moreover, since the terminal 146 of the electrical member 140 is spaced apart from the connection port 110, the connection port 110 can move with the skin S without transmitting any forces from such movement to the electrical member 140. Said another way, this arrangement allows the connection port 110 and the electrical member 140 to be electrically coupled while remaining mechanically isolated.

The distal end portion 142 of the electrical member 140 includes a terminal 147 that is disposed adjacent the target tissue T within the body. In some embodiments, for example, the terminal 147 can include one or more electrodes configured to be disposed about the target tissue T (e.g., a cuff electrode) such that an electrical signal can be conveyed between the terminal 147 of the electrical member 140 and the target tissue T.

The stimulation system 100 can be used as described in U.S. Patent Publication No. 2006/0184211, entitled "Method of Routing Electrical Current to Bodily Tissues Via Implanted Passive Conductors," filed Jan. 23, 2006, which is incorporated herein by reference in its entirety. In some embodiments, for example, the stimulation system 100 can be used to deliver electrical stimulation from the electrical device 130 through the skin S via the connecting port 110 to the target tissue T to treat a medical condition. For example, in some embodiments, the stimulation system can be used for pain treatment (e.g., pain resulting from carpal tunnel syndrome, arthritis, traumatic injury or the like), muscle rehabilitation, or the like.

In some embodiments, for example, the electrical device 130 can produce an electrical current having characteristics suitable for therapeutic stimulation. For example, in some embodiments, the electrical device 130 can produce a pulsed electrical current having an amplitude of approximately 1 mA and a pulse frequency of approximately 50 pulses per second. The electrical current can be conveyed from the electrical device 130 to the proximal end 111 of the connection port 110 via the connection wire 132.

As described above, the stud 116 defines an electrically conductive pathway 126 such that the electrical signal can be conveyed from the proximal end 111 of the connection port 110 to the distal end 112 of the connection port 110. The electrically conductive pathway 126 of the connection port 110 is characterized by an electrical impedance less than an electrical impedance of the skin S. In this manner, the electrical signal, which can be, for example an electrical current, can be conveyed from an area outside of the body B through the skin S without significant attenuation. Said another way, the electrical signal can be conveyed from an area outside of the body B through the skin S via an electrical pathway that excludes the skin S.

The electrical signal can then be conveyed from the distal end portion 112 of the connection port 110 to the terminal 146 of the electrical member 140 by the electrical coupling. The electrical signal can then be conveyed via the electrically conductive pathway defined by the electrical member 140 from the terminal 146 to the terminal 147. In this manner, the electrical signal can be conveyed from the electrical device 130 to the target tissue T within the body B without significant attenuation. Said another way, this arrangement allows the electrical signal produced by the electrical device 130 to be conveyed to the target tissue T via a stimulation path (not shown in FIG. 1) that excludes the skin S.

The connection port 110 can be any suitable shape and size to facilitate percutaneous insertion of the connection port 110 within the body B. For example, in some embodiments, the stud 116 of the connection port 110 can be cylindrically shaped having a diameter of between 1 mm and 3 mm. In other embodiments, the stud 116 of the connection port 110 can have a diameter of approximately 1 mm. Similarly, in some embodiments, the anchor 120 can be disc-shaped (e.g., the anchor 120 can be substantially circular about the longitudinal axis $A_L$ of the stud 116) having a diameter of between 10 mm and 30 mm and a thickness of between 1 mm and 3 mm. In other embodiments, the anchor 120 can be disc-shaped having a diameter of approximately 20 mm and a thickness of approximately 2 mm.

The connection port 110 can be constructed from any material or combination of materials having suitable properties. Such suitable material properties include biocompatibility, electrical conductivity and/or impedance, mechanical strength, or the like. For example, in some embodiments, the connection port 110 can be constructed from a rigid material. In other embodiments, the connection port 110 can be constructed from a flexible material configured to deform when the connection port 110 is disposed within the body B. Similarly, in some embodiments, the connection port 110 can be monolithically constructed. In other embodiments, the connection port 110 can be an assembly of separately formed components.

In some embodiments, the connection port 110 and/or the stud 116 of the connection port 110 can be constructed from a conductive material. In this manner, the electrically conductive pathway 126 can include the entirety of the connection port 110 and/or the stud 116. Such conductive materials can have an electrical conductivity greater than an electrical conductivity of the skin S and/or the subcutaneous tissue beneath the skin S. Such conductive materials can include, for example, titanium, pyrolytic carbon, stainless steel, platinum, iridium, carbon and any suitable combination thereof. In some embodiments, for example, the connection port 110 can be constructed from titanium plated with a layer of platinum, iridium, pyrolytic carbon, vapor deposited carbon, or the like to prevent oxidization of the titanium to improve the electrical conductivity of the connection port 110.

In some embodiments, the connection port 110 can include both electrically conductive materials and electrically insulative materials. For example, in some embodiments, the stud 116 can include a first portion (not shown in FIG. 1) and a second portion (not shown in FIG. 1). The first portion can be constructed from an electrically insulative material such as, for example, a rigid epoxy, polycarbonate, silicone, polytetrafluroethylene, polypropylene, polyurethane and polysulfone (PSU). The second portion can be constructed from an electrically conductive material and can extend from the connecting surface 117 to the terminal surface 127. In this manner, the second portion can define the electrically conductive pathway 126 between the connection surface 117 and the terminal surface 127. In some embodiments, the second portion can be, for example, a wire disposed within the electrically insulative material. In other embodiments, the second portion can be, for example, a plating about the first portion of the stud 116.

Figure 2:
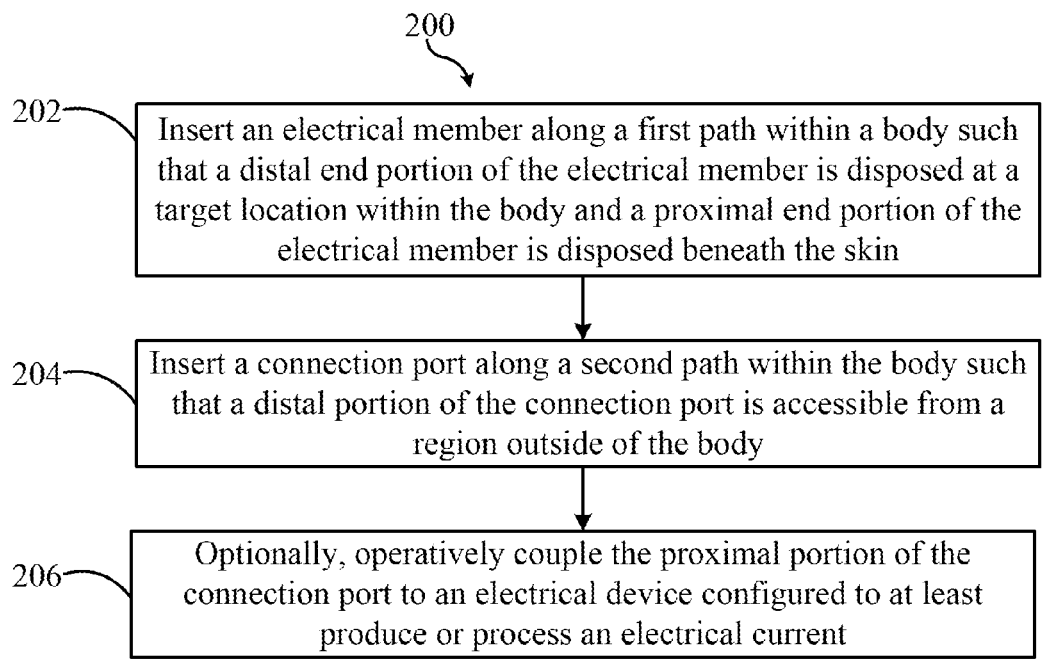
FIG. 2 is a flow chart of a method of inserting the stimulation system shown in FIG. 1 into the body.
Figure 3:
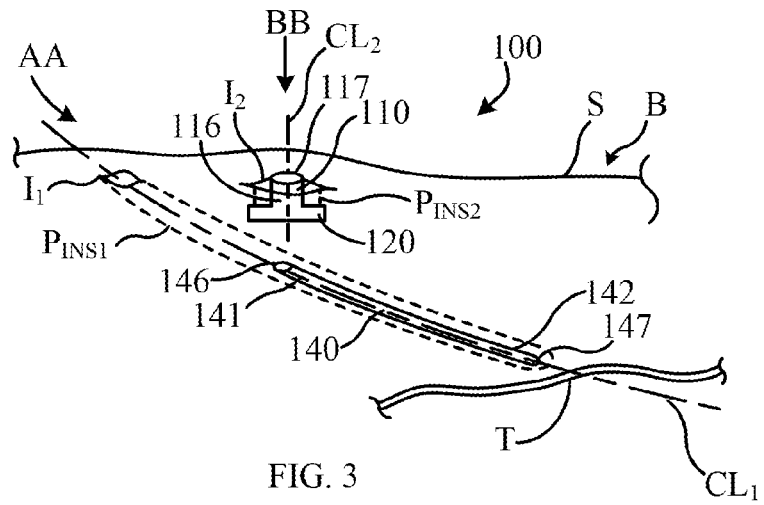
FIG. 3 is a schematic illustration showing a method of inserting the stimulation system shown in FIG. 1 into the body.

FIG. 2 is a flow chart of a method 200 of disposing the stimulation system 100 within the body B according to an embodiment of the invention. The method illustrated in FIG. 2 is discussed with reference to FIG. 3, which is a schematic illustration of the stimulation system 100 disposed within the body B. The method includes inserting an electrical member along a first insertion path within the body such that a proximal end of the electrical member is disposed beneath the skin of the body, 202. Referring to FIG. 3, the electrical member 140 is inserted into the body B through an incision $I_1$, as shown by arrow AA. The electrical member 140 is moved along the first insertion path $P_{INS1}$ (represented by dashed lines in FIG. 3) within the body B such that the proximal end 141 of the electrical member 140 is disposed beneath the skin S of the body B. Said another way, the electrical member 140 is inserted along a first insertion path $P_{INS1}$ within the body B until the electrical member 140 is disposed entirely within the body B. In some embodiments, the distal end 142 of the electrical member 140 is disposed adjacent the target tissue T, which can be, for example, a nerve, a muscle, and/or the like.

In some embodiments, the electrical member 140 is inserted percutaneously. In other embodiments, inserting the electrical member 140 can include dilating a bodily tissue and/or forming the first insertion path $P_{INS1}$. For example, in some embodiments, the distal end 142 of the electrical member 140 can be configured to dilate a portion of the body B. In other embodiments, the first insertion path $P_{INS1}$ can be formed by a separate tool, such as for example, an insertion probe, a trocar or the like.

Returning to the flow chart shown in FIG. 2, a connection port is inserted along a second insertion path within the body such that a proximal portion of the connection port is accessible from a region outside of the body, 204. In some embodiments, for example, the connection port can be inserted such that a distal portion of the connection port is spaced apart from and operatively coupled to the proximal end portion of the electrical member, 204. Referring to FIG. 4, the connection port 110 is inserted into the body B through an incision $I_2$, as shown by arrow CC. The connection port 110 is moved along the second insertion path $P_{INS2}$ (represented by dashed lines in FIG. 3) within the body B such that the anchor 120 is disposed subcutaneously within the body B. In this manner, as described above, the anchor 120 can maintain a location of the connection port 110 within the body B.

The distal portion 112 of the connection port 110 can be operatively coupled to the proximal end portion 141 of the electrical member 140 by any suitable means. Said another way, the distal portion 112 of the connection port 110 can be electrically coupled to the electrical member 140 by any suitable means that permits the connection port 110 and the electrical member 140 to be spaced apart. For example, in some embodiments, the connection port 110 can be electrically coupled to the electrical member 140 by a galvanic coupling. In other embodiments, the connection port 110 can be electrically coupled to the electrical member 140 by a capacitive coupling. In yet other embodiments, the connection port 110 can be electrically coupled to the electrical member 140 by an inductive coupling. In still other embodiments, the connection port 110 can be electrically coupled to the electrical member 140 by a radio frequency coupling or any other suitable wireless coupling.

As shown in FIG. 3, the first insertion path $P_{INS1}$ is different from the second insertion path $P_{INS2}$. For example, in some embodiments, a center line $CL_1$ of the first insertion path $P_{INS1}$ can be angularly offset from a center line $CL_2$ of the second insertion path $P_{INS2}$. Said another way, in some embodiments, the trajectory of the first insertion path $P_{INS1}$ can be different than a trajectory of the second insertion path $P_{INS2}$. In this manner, the first incision $I_1$ can be disposed apart from the second incision $I_2$. This arrangement can allow the first incision $I_1$ and/or the second incision $I_2$ to be located on the body B in an inconspicuous location. Moreover, by inserting the electrical member 140 and the connection port 110 via distinct insertion paths, the first insertion path $P_{INS1}$ can have a different size (e.g., diameter and/or depth) than the second insertion path $P_{INS2}$. In this manner, the first insertion path $P_{INS1}$ can be defined based solely on the characteristics of the electrical member 140. Similarly, the second insertion path $P_{INS2}$ can be defined based solely on the characteristics of the connection port 110.

Returning to FIG. 2, in some embodiments, the method can optionally include operatively coupling the proximal portion of the connection port to an electrical device, 206. In some embodiments, the electrical device can be disposed outside of the body. In some embodiments, for example, the electrical device can be a stimulator disposed outside of the body configured to at least produce or process an electrical signal. In other embodiments, the electrical device can be a signal-processor.

Figure 4A:
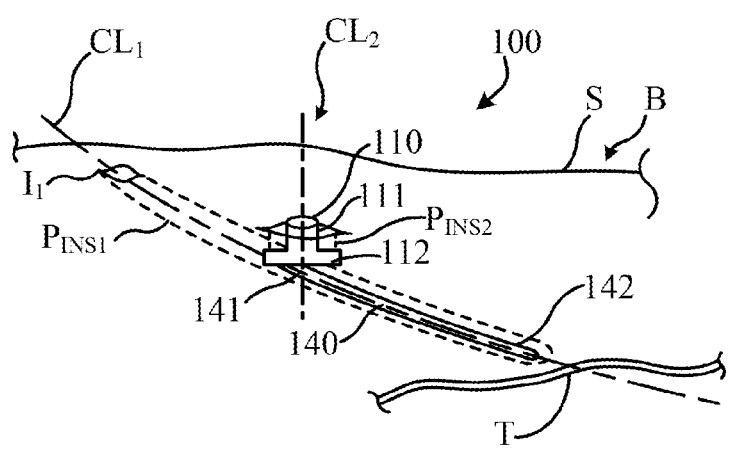
FIG. 4A is a schematic illustration showing a method of inserting the stimulation system shown in FIG. 1 into the body.

Although the distal portion 112 of the connection port 110 is shown and described above as being spaced apart from the proximal end portion 141 of the electrical member 140, in some embodiments, the distal portion 112 of the connection port 110 can be in contact with, engaged with and/or mechanically coupled to the proximal end portion 141 of the electrical member 140. For example, FIG. 4A is a schematic illustration of the stimulation system 100 disposed within the body B according to an embodiment of the invention. The arrangement of the stimulation system 100 within the body B differs from the arrangement of the stimulation system 100 within the body B as shown in FIG. 3 in that the connection port 110 is in contact with the proximal end portion 141 of the electrical member 140. This arrangement can be achieved, for example, by inserting the connection port 110 along the second insertion path $P_{INS2}$ until the distal end 112 of the connection port 110 touches the proximal end portion 141 of the electrical member 140.

In other embodiments, the connection port 110 can be coupled to the proximal end portion 141 of the electrical member 140 prior to the connection port 110 and/or the electrical member 140 being inserted into the body B. For example, FIGS. 4B-4D are schematic illustrations of a method of inserting the stimulation system 100 into the body B according to an embodiment of the invention. As shown in FIG. 4B, the electrical member 140 is inserted into the body B through an incision $I_1$, as shown by arrow DD. The electrical member 140 is moved along the first insertion path $P_{INS1}$ (represented by dashed lines in FIG. 4B) within the body B such that the proximal end 141 of the electrical member 140 is disposed beneath the skin S of the body B. In some embodiments, the distal end 142 of the electrical member 140 is disposed adjacent the target tissue T, which can be, for example, a nerve, a muscle, and/or the like.

As shown in FIG. 4C, the connection port 110 is inserted into the body B through the incision $I_1$, as shown by arrow EE. The connection port 110 is moved within the body B along the second insertion path $P_{INS2}$ (represented by dashed lines in FIG. 4B) within the body B. Although the proximal portion 111 of the connection port 110 is shown as being moved along the second insertion path $P_{INS2}$ first, in other embodiments, the connection port can be moved along the second insertion path $P_{INS2}$ with the distal portion 112 first.

As shown in FIG. 4D, the proximal portion 111 of connection port 110 is then disposed through the skin S, as shown by the arrow FF. In this manner, the connection port 110 is disposed within the body B such that the anchor 120 is disposed subcutaneously within the body B and the terminal surface 117 of the proximal portion 111 is accessible from a region outside of the body B. Accordingly, as described above, the anchor 120 can maintain a location of the connection port 110 within the body B. Said another way, the proximal portion 111 of connection port 110 is then disposed through the skin S to define the second incision $I_2$.

Although the stimulation system 100 is shown in FIG. 4A as being inserted via two insertion pathways (i.e., $P_{INS1}$ and $P_{INS2}$), in other embodiments, the stimulation system 100 can be inserted via a single insertion pathway. For example, in some embodiments, the distal end 112 of the connection port 110 can be coupled to the proximal end portion 141 of the electrical member 140 prior to insertion, and the assembly can then be inserted via a single insertion pathway. The distal end 112 of the connection port 110 can be coupled to the proximal end portion 141 of the electrical member 140 by any suitable means. For example, in some embodiments, the distal end 112 of the connection port 110 can be coupled to the proximal end portion 141 of the electrical member 140 by a connective adhesive, a magnetic coupling, welding, soldering and/or crimping.

Although the stimulation system 100 is shown and described as having one connection port 110 percutaneously disposed within the body B, in some embodiments, a stimulation system can have multiple connection ports percutaneously disposed within the body. In yet other embodiments, a stimulation system can have one or more connection ports percutaneously disposed within the body and one or more surface electrodes disposed on the surface of the body. In yet other embodiments, the connection port may have several distinct electrically conductive pathways.

Figure 5:
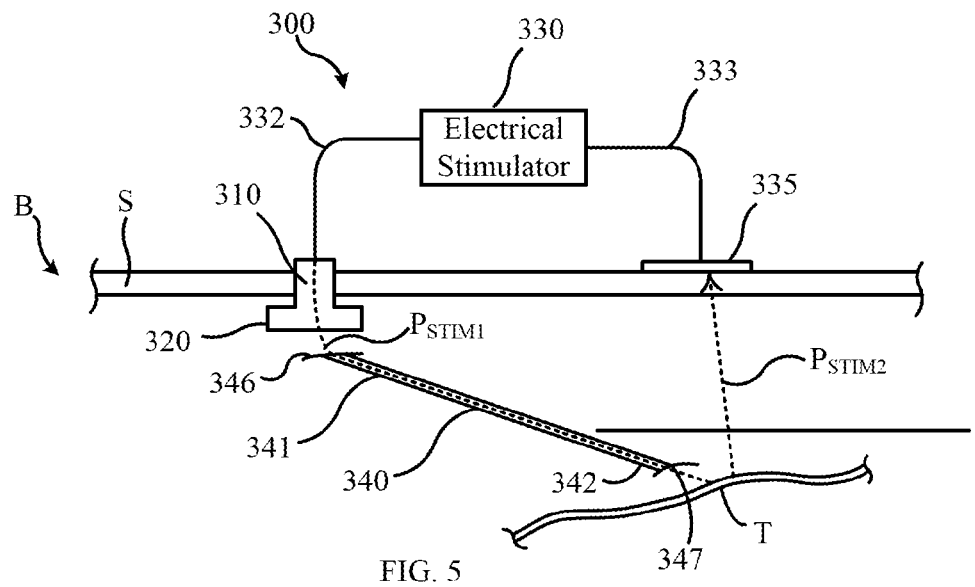
FIG. 5 is a schematic illustration of a stimulation system according to an embodiment of the invention disposed within a body.

For example, FIG. 5 is a schematic illustration of a stimulation system 300 according to an embodiment of the invention disposed within a body B. The stimulation system 300 includes an electrical stimulator 330 disposed outside of the body B, an electrical member 340 disposed within the body B, a connection port 310, and a surface electrode 335. The connection port 310, which can act as a cathodic electrode, is similar to the connection port 110 shown and described above. The connection port 310 is disposed within the body B such that an anchor 320 of the connection port 310 is disposed subcutaneously to maintain a location of the connection port 310 within the body B. The connection port 310 is electrically coupled to the electrical stimulator 330 by a connection wire 332. The connection port 310 is electrically coupled to (e.g., by a galvanic coupling) and spaced apart from the electrical member 340.

As described above, the electrical member 340 has a proximal end portion 341 and a distal end portion 342, and defines an electrically conductive path therethrough. The proximal end portion 341 of the electrical member 340 includes a terminal 346 that is spaced apart from and operatively coupled to the connection port 310. The distal end portion 342 of the electrical member 340 includes a terminal 347 that is disposed adjacent the target tissue T within the body. In this manner, an electrical signal, such as, for example, an electrical current, can be conveyed from the electrical stimulator 330 to a target tissue T (e.g., neural tissue) within the body B via the connection port 310. Moreover, the electrical current can be conveyed from the electrical stimulator 330 to the target tissue T within the body B via an electrical pathway that excludes the skin S.

The surface electrode 335, which can act as an anodic electrode, is disposed on the surface of the skin S. The location of the surface electrode 335 on the surface of the skin S can be maintained by any suitable means, such as, for example, a conductive gel, adhesive, a wetted electrode, a fitted garment or the like. The surface electrode 335 is electrically coupled to the electrical stimulator 330 by a connection wire 333. The surface electrode 335 can be any suitable electrode for transmitting and/or receiving an electrical signal to or from the body B. For example, in some embodiments, the surface electrode 335 can be a gel electrode. In other embodiments, the surface electrode 335 can be a flexible disc-type electrode having electrical leads. Similarly, the surface electrode 335 can be constructed from any suitable material, such as, for example, conductive electrolyte gel, conductive rubber, conductive plastic, metal mesh, metal plate, metallized rubber and/or plastic.

In use, the electrical stimulator 330 can produce an electrical current having characteristics suitable for therapeutic stimulation. The electrical current flows along a first stimulation path $P_{STIM1}$ (represented by dashed lines in FIG. 5) within the body B, which includes the connecting port 310, the electrical member 340 and the subcutaneous body tissue therebetween. In this manner, at least a portion of the electrical current can be conveyed from the electrical stimulator 330 to the target tissue T. The portion of electrical current can then be returned to the surface electrode 335 via a second stimulation path $P_{STIM2}$ (represented by dashed lines in FIG. 5) within the body, which includes subcutaneous body tissue and the skin.

Although the stimulation system 300 is shown and described as including one cathodic electrode (i.e., connection port 310) and one anodic electrode (i.e., surface electrode 335), in some embodiments, a stimulation system can include at least one electrode and/or connection port that can function as both a cathodic electrode and an anodic electrode. In other embodiments, a stimulation system can include multiple surface electrodes and/or connection ports configured to function as multiple pairs of cathodic electrodes and/or multiple anodic electrodes. In this manner, a stimulation system according to an embodiment of the invention can convey an electrical current into the body via more than one stimulation path.

Moreover, although the stimulation systems shown and described above include an electrical member disposed entirely within the body (e.g., a passive electrical conductor, an electrical device or the like), in some embodiments, a stimulation system can be devoid of an electrical member disposed entirely within the body. For example, in some embodiments, a stimulation system can include an electrical stimulator and a connection port of the types shown and described above. In such stimulation systems, an electrical signal can be conveyed from the electrical stimulator to a target tissue via a stimulation path that excludes the skin and includes subcutaneous body tissue.

Figure 6:
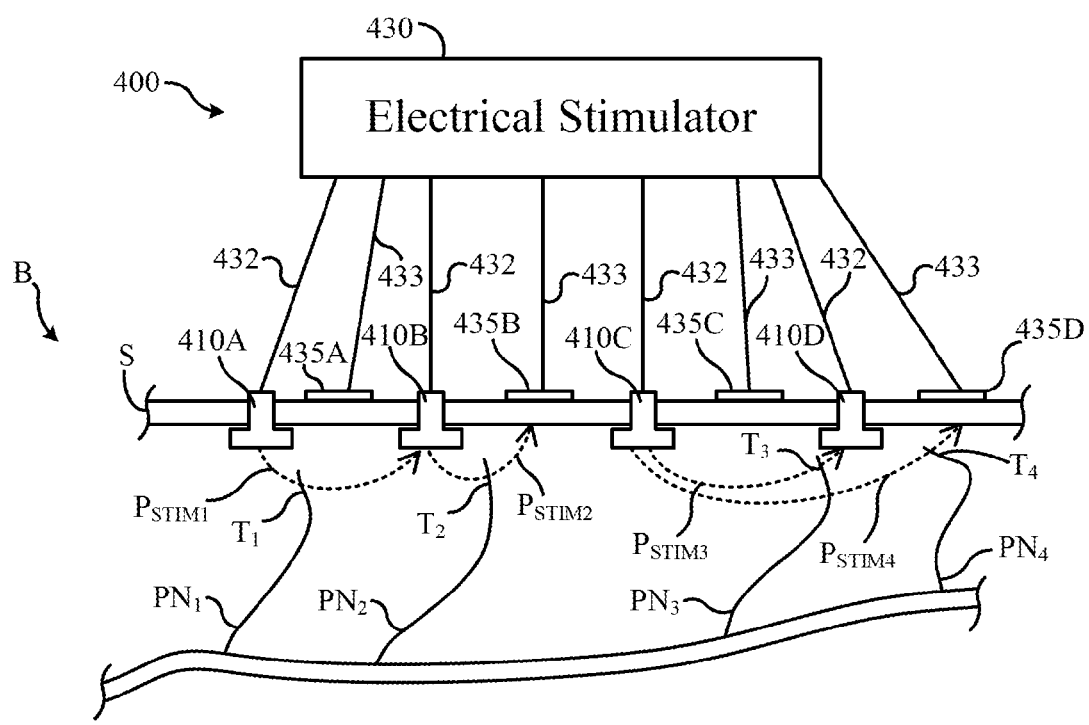
FIG. 6 is a schematic illustration of a stimulation system according to an embodiment of the invention disposed within a body.

For example, FIG. 6 is a schematic illustration of a stimulation system 400 according to an embodiment of the invention disposed within a body B. The stimulation system includes an electrical stimulator 430 disposed outside of the body B, four connecting ports 410A-410D, and four surface electrodes 435A-435D. The connection ports 410A-410D, which are similar to the connection ports shown and described above, are electrically coupled to the electrical stimulator 430 by a series of connection wires 432. The surface electrodes 435A-435D, which are similar to the connection ports shown and described above, are electrically coupled to the electrical stimulator 430 by a series of connection wires 433. In some embodiments, the stimulation system 400 can include a multiplexer (not shown in FIG. 7) to allow at least a first pair of connection ports 410A-410D and/or surface electrodes 435A-435D to be electrically coupled to the electrical stimulator 430 while electrically isolating at least a second pair of connection ports 410A-410D and/or surface electrodes 435A-435D. In this manner, as described below, the array of connection ports 410A-410D and surface electrodes 435A-435D can be used to define multiple different stimulation paths within the body B. Moreover, the multiplexer can be configured to electrically couple the connection ports 410A-410D and/or surface electrodes 435A-435D to deliver either bipolar stimulation or monopolar stimulation.

For example, the stimulation system 400 can be placed in a first configuration in which the electrical stimulator 430 is electrically coupled to the first connection port 410A and the second connection port 410B. The electrical stimulator 430 produces an electrical current having characteristics suitable for therapeutic stimulation, as described above. The electrical current can flow from the electrical stimulator 430 to the first connection port 410A. The current can then be conveyed within the body B via a first stimulation path $P_{STIM1}$, which terminates at the second connection port 410B. In this manner, the electrical current can be conveyed from the electrical stimulator 430 to a first target tissue $T_1$, which can include, for example, a first peripheral nerve $PN_1$.

As shown in FIG. 6, the stimulation system 400 can be placed in a second configuration in which the electrical stimulator 430 is electrically coupled to the second connection port 410B and the second surface electrode 435B. An electrical current from the electrical stimulator 430 can flow from the electrical stimulator 430 to the second connection port 410B. The current can then be conveyed within the body B via a second stimulation path $P_{STIM2}$, which terminates at the second surface electrode 435B. In this manner, the electrical current can be conveyed from the electrical stimulator 430 to a second target tissue $T_2$, which can include, for example, a second peripheral nerve $PN_2$.

Similarly, the stimulation system 400 can be placed in a third configuration in which the electrical stimulator 430 is electrically coupled to the third connection port 410C and the fourth connection port 410D. An electrical current from the electrical stimulator 430 can flow from the electrical stimulator 430 to the third connection port 410C. The current can then be conveyed within the body B via a third stimulation path $P_{STIM3}$, which terminates at the fourth connection port 410D. In this manner, the electrical current can be conveyed from the electrical stimulator 430 to a third target tissue $T_3$, which can include, for example, a third peripheral nerve $PN_3$.

Similarly, the stimulation system 400 can be placed in a fourth configuration in which the electrical stimulator 430 is electrically coupled to the third connection port 410C and the fourth surface electrode 435D. An electrical current from the electrical stimulator 430 can flow from the electrical stimulator 430 to the third connection port 410C. The current can then be conveyed within the body B via a fourth stimulation path $P_{STIM4}$, which terminates at the fourth surface electrode 435D. In this manner, the electrical current can be conveyed from the electrical stimulator 430 to a fourth target tissue $T_4$, which can include, for example, a fourth peripheral nerve $PN_4$.

In a similar manner, any combination surface electrodes 435A-435D can be selected to convey an electrical current (either monopolar or bipolar) within the body B to any combination of connection ports 410A-410B. Similarly, any combination of connection ports 410A-410D can be selected to convey an electrical current within the body to stimulate one or more target tissues $T_1$-$T_4$. Said another way, the array of connection ports 410A-410D and/or surface electrodes 435A-435D can be selectively used to stimulate specific areas of target body tissue.

The selection of the connection ports 410A-410D and/or the surface electrodes 435A-435D can be performed manually by iteratively electrically coupling pairs of the connection ports 410A-410D and/or the surface electrodes 435A-435D to the electrical stimulator 430 and measuring the patient's response to determine the desired selections. Alternatively, in some embodiments, the stimulation system 400 can include a processor configured to automatically select and electrically couple the connection ports 410A-410D and/or the surface electrodes 435A-435D to the electrical stimulator 430. For example, in some embodiments, the stimulation system 400 can include a processor configured to automatically select and/or electrically couple the connection ports 410A-410D and/or the surface electrodes 435A-435D to the electrical stimulator 430 based on the impedance between the various combinations of the connection ports 410A-410D and/or the surface electrodes 435A-435D. In other embodiments, the stimulation system 400 can include a processor configured to automatically select and/or electrically couple the connection ports 410A-410D and/or the surface electrodes 435A-435D based on a measured response from the patient (e.g., a muscle response, and or verbal response) and/or a direct input by a user (e.g., an input independent from the patient's response).

Figure 7:
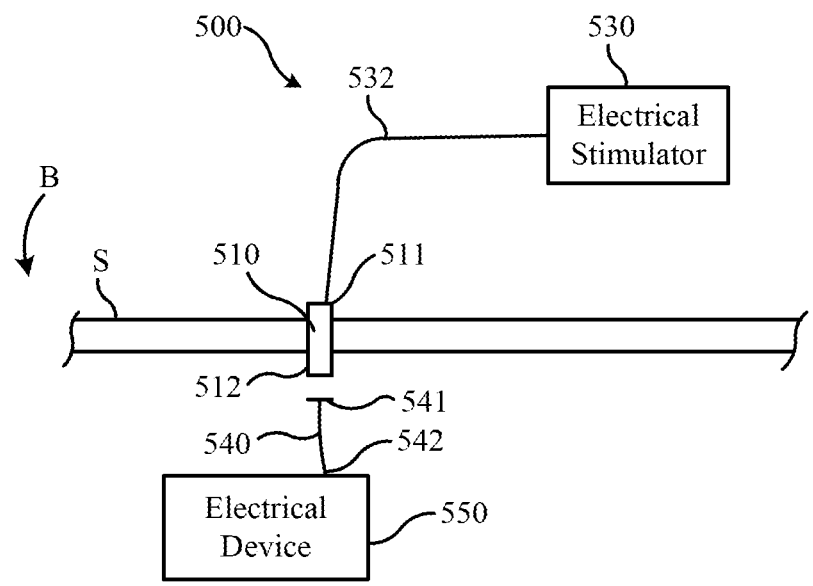
FIG. 7 is a schematic illustration of a stimulation system according to an embodiment of the invention disposed within a body.

Although the stimulation systems are shown and described above as being configured to convey an electrical current to stimulate a target tissue within the body, in some embodiments, a stimulation system can be configured to convey an electrical signal to an electrical device disposed within the body. For example, FIG. 7 is a schematic illustration of a stimulating system 500 according to an embodiment of the invention disposed within a body B. The stimulating system 500 includes an electrical stimulator 530 disposed outside of the body B, an electrical member 540 disposed within the body B, an electrical device 550 disposed within the body, and a connection port 510. The connection port 510, which is similar to the connection ports shown and described above, is disposed within the body B such that a distal portion 512 of the connection port 510 is disposed subcutaneously within the body B adjacent the electrical member 540. A proximal portion 511 of the connection port 510 is electrically coupled to the electrical stimulator 530 by a connection wire 532.

As described above, the electrical member 540 has a proximal end portion 541 and a distal end portion 542, and defines an electrically conductive path therethrough. The proximal end portion 541 is spaced apart from and operatively coupled to the connection port 510 (e.g., by a galvanic coupling). The distal end portion 542 of the electrical member 540 is electrically coupled to the electrical device 550. In this manner, an electrical signal can be conveyed from the electrical stimulator 530 to the electrical device 550 within the body B via the connection port 510. Moreover, the electrical signal can be conveyed from the electrical stimulator 530 to the electrical device 550 via an electrical pathway that excludes the skin S.

The electrical device 550 can be any electrical device powered by electrical current and/or any electrical device that receives an electrical signal. For example, in some embodiments, the electrical device 550 can be a sensor implanted within the body B to assess intra-body parameters. Such sensors can include, for example, electroneurogram (ENG) sensors, electromyogram (EMG) sensors, electrocardiogram (ECG) sensors, temperature sensors, pressure sensors, pH sensors, tilt sensors, accelerometers, gyroscopes, displacement sensors, and/or impedance sensors. In other embodiments, the electrical device 550 can be a portion of an electrical circuit implanted within the body B, such as, for example, an amplifier, a filter, a high voltage/constant current generator, an electrical switch, a power supply, a battery (including a miniature rechargeable battery), a battery-charging circuit, a processor, a frequency shifter, an over-stimulation protection circuit, and/or a communication module (wired or wireless).

In use, the electrical stimulator 530 produces an electrical signal (e.g., an electrical current) having characteristics associated with the electrical device 550. The electrical signal can be conveyed from the electrical stimulator 530 to the electrical device 550 within the body B via the connection port 510 via an electrical pathway that excludes the skin S. Accordingly, since the electrical signal does not pass through the skin S, the electrical signal can have any amplitude and/or frequency that is not harmful to the subcutaneous body tissues.

Figure 8:
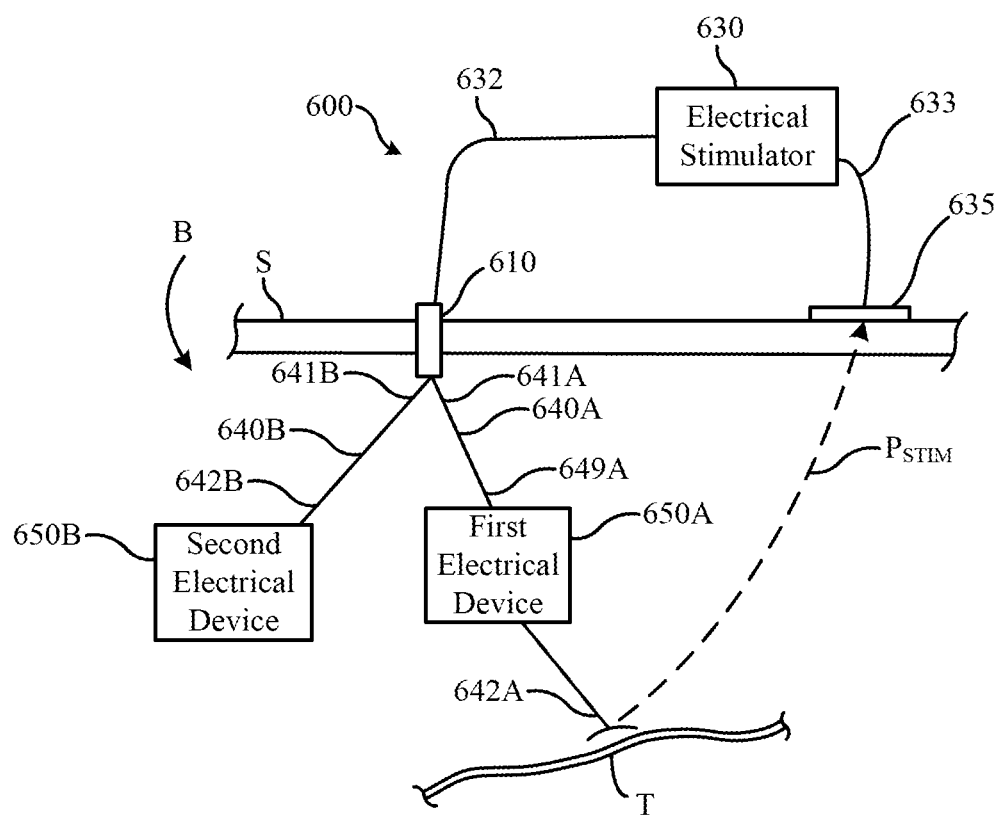
FIG. 8 is a schematic illustration of a stimulation system according to an embodiment of the invention disposed within a body.

Although the stimulation system 500 is shown as including a single electrical device 550 coupled to the distal end portion 542 of the electrical member 540, in other embodiments, the electrical device 550 can be coupled to any portion of the electrical member 540. In yet other embodiments, a stimulation system can include multiple electrical devices 550 and/or multiple electrical members 540. For example, FIG. 8 is a schematic illustration of a stimulating system 600 according to an embodiment of the invention disposed within a body B. The stimulating system 600 includes an electrical stimulator 630 disposed outside of the body B, a first electrical member 640A and a second electrical member 640B each disposed within the body B, a first electrical device 650A and a second electrical device 650B each disposed within the body B, a connection port 610, and a surface electrode 635. The connection port 610, which is similar to the connection ports shown and described above, is disposed within the body B such that a distal portion 612 of the connection port 610 is disposed subcutaneously within the body B adjacent the electrical member 640. The connection port 610 is electrically coupled to the electrical stimulator 630 by a connection wire 632.

The surface electrode 635 is disposed on the surface of the skin S and is electrically coupled to the electrical stimulator 630 by a connection wire 633. As described above, the surface electrode 635 can be any suitable electrode for transmitting and/or receiving an electrical signal to or from the body B.

The first electrical member 640A has a proximal end portion 641A, a distal end portion 642A, and a central portion 649A, and defines an electrically conductive path therethrough. The proximal end portion 641A of the first electrical member 640A is electrically coupled to the connection port 610. The central portion 649A of the first electrical member 640A is electrically coupled to the first electrical device 650A. The distal end portion 642A of the first electrical member 640A is disposed adjacent the target tissue T within the body. In this manner, an electrical signal can be conveyed from the electrical stimulator 630 to the first electrical device 650A and then to the target tissue T via the connection port 610. Said another way, this arrangement allows the electrical signal to be conveyed to the first electrical device 650A and the target tissue T in series. As described above, the electrical signal can be returned to the surface electrode 635 via a stimulation path $P_{STIM}$, which includes body tissue.

The second electrical member 640B has a proximal end portion 641B and a distal end portion 642B, and defines an electrically conductive path therethrough. The proximal end portion 641B of the second electrical member 640B is electrically coupled to the connection port 610 in parallel with the first electrical member 640A. The distal end portion 642B of the second electrical member 640B is electrically coupled to the second electrical device 650B. In this manner, an electrical signal can be conveyed from the electrical stimulator 630 to the second electrical device 650B in parallel with the stimulation of the target tissue T.

Figure 9:
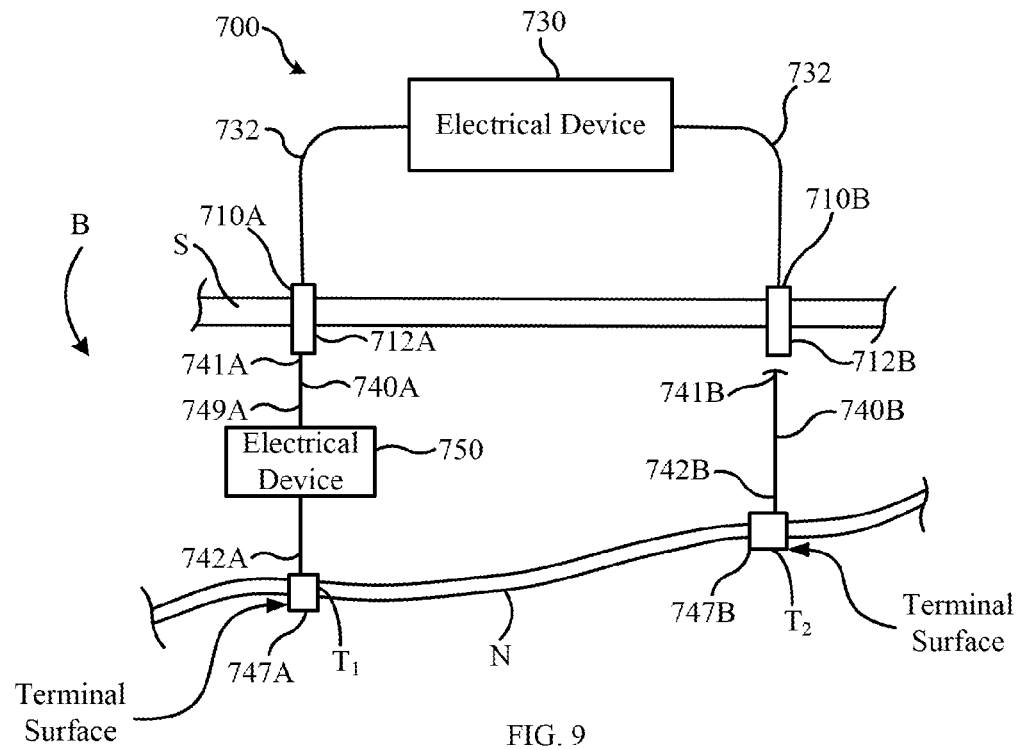
FIG. 9 is a schematic illustration of a stimulation system according to an embodiment of the invention disposed within a body.

Although the stimulation systems are shown and described above as conveying an electrical signal to a target tissue and/or an implanted electrical device, in other embodiments, a medical system can receive an electrical signal from a target tissue and/or an implanted electrical device. Such electrical signals can include, for example, monopolar and bi-polar signals from a neural tissue within the body (e.g., an electroneurogram or ENG signal). For example, FIG. 9 is a schematic illustration of a medical system 700 according to an embodiment of the invention disposed within a body B. The medical system 700 includes an electrical device 730 disposed outside of the body B, a first electrical member 740A and a second electrical member 740B, an electrical device 750 disposed inside of the body, a first connection port 710A, and a second connection port 710B.

The first connection port 710A, which is similar to the connection ports shown and described above, is disposed within the body B such that a distal portion 712A of the first connection port 710A is disposed subcutaneously within the body B adjacent the first electrical member 740A. The first connection port 710A is electrically coupled to the electrical device 730 by a connection wire 732. Similarly, the second connection port 710B is disposed within the body B such that a distal portion 712B of the second connection port 710B is disposed subcutaneously within the body B adjacent the second electrical member 740B. The second connection port 710B is electrically coupled to the electrical device 730 by a connection wire 732.

The electrical device 730 disposed outside of the body B can be any electrical device configured to receive and/or process an electrical signal. In some embodiments, the electrical device can be a signal processor. In other embodiments, the electrical device can be an electrical data recorder, such as, for example, a datalogger, a strip chart recorder, or the like. The electrical device 750 disposed inside of the body B can be any electrical device configured to be implanted within the body, such as, for example, a sensor, an amplifier, a filter, a communication module or the like.

The first electrical member 740A has a proximal end portion 741A, a distal end portion 742A, and a central portion 749A, and defines an electrically conductive path therethrough. The proximal end portion 741A of the first electrical member 740A is electrically coupled to the first connection port 710A. The central portion 749A of the first electrical member 740A is electrically coupled to the electrical device 750 disposed within the body B. The distal end portion 742A of the first electrical member 740A includes a terminal surface 747A (e.g., an electrical pick-up) disposed adjacent or about a first target tissue $T_1$ within the body B. The first target tissue $T_1$ can be, for example, a first location on a nerve N.

The second electrical member 740B has a proximal end portion 741B and a distal end portion 742B, and defines an electrically conductive path therethrough. The proximal end portion 741B of the second electrical member 740B is electrically coupled to the second connection port 710B. The distal end portion 742B of the second electrical member 740B includes a terminal surface 747B (e.g., an electrical pick-up) disposed adjacent a second target tissue $T_2$ within the body B. The second target tissue $T_2$ can be, for example, a second location on the nerve N, spaced apart from the first location.

In use, the terminal surfaces 747A and 747B can receive a first electrical signal and a second electrical signal, respectively, produced by the nerve N. The first electrical signal can be conveyed from the terminal surface 747A to the electrical device 750 disposed within the body B via the electrical member 740A. In some embodiments, the electrical device 750 can process the first electrical signal, for example, by amplifying the signal, processing the signal and/or the like. In this manner, the quality of the first electrical signal can be improved prior to its conveyance to the electrical device 730 outside of the body B. The resulting first electrical signal can then be conveyed to the electrical device 730 disposed outside of the body B via the first connection port 710A. Similarly, the second electrical signal can be conveyed from the terminal surface 747B to the electrical device 730 disposed outside of the body B via the second connection port 710B.

Figure 10:
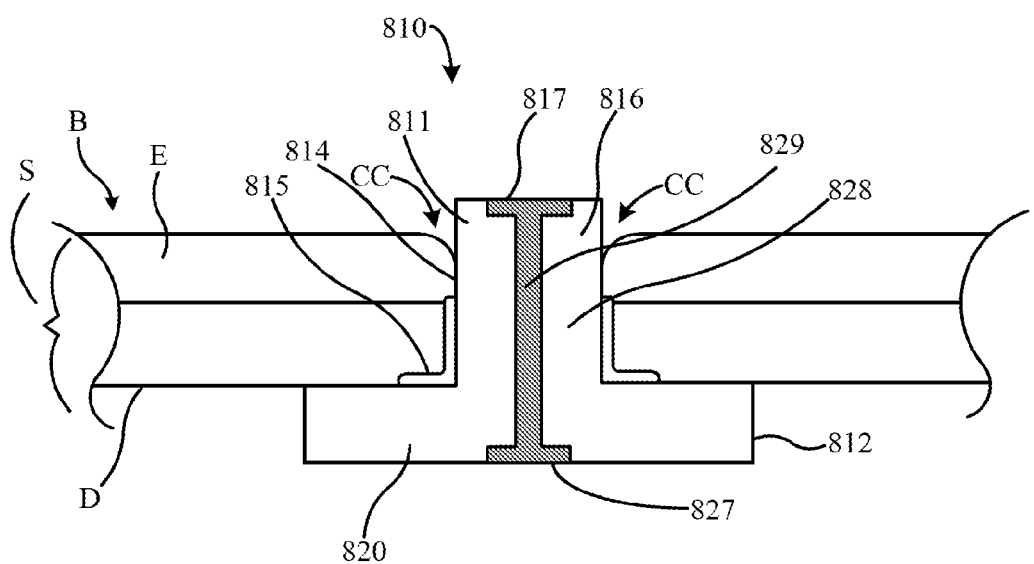
FIG. 10 is a front view of a medical device according to an embodiment of the invention disposed within a body.

In some embodiments, the connection ports shown and described above can be constructed from biocompatible materials that bond with living tissue (e.g., the dermis and/or epidermis) to form a seal. For example, FIG. 10 is a schematic illustration of a connection port 810 according to an embodiment of the invention disposed percutaneously within a body B. The connection port 810 includes a stud 816 and an anchor 820, and has a proximal portion 811 and a distal portion 812. The proximal portion 811 includes a connection surface 817. The distal portion 812 includes a terminal surface 827. The stud 816 includes an outer portion 828 constructed from a first material having a first electrical conductivity, and an inner portion 829 constructed from a second material having a second electrical conductivity greater than that of the first material. In this manner, the inner portion 829 defines an electrically conductive pathway 826 between the connection surface 817 and the terminal surface 827.

As described above, the anchor 820 is disposed at the distal portion 812 of the connection port 810 and is disposed beneath the skin S of the body B. The anchor 820 extends outwardly from the stud 816 to anchor the connection port 810 in a subcutaneous location within the body B.

At least a portion of an outer surface 814 of the connection port 810 is covered with a fibrous and/or porous layer 815 configured to promote ingrowth of soft bodily tissue around the outer surface 814 of the stud 816 and/or the anchor 820. The fibrous and/or porous layer 815 is disposed about the portion of the outer surface 814 such that when the connection port 810 is implanted, the fibrous and/or porous layer 815 is disposed within the dermis D of the skin S. In this manner, the fibrous and/or porous layer 815 can block the downward growth of the epidermis E (as indicated by the arrows CC in FIG. 10) and/or promote bonding of the dermis D to the connection port 810. Said another way, the fibrous and/or porous layer 815 can limit the body's natural propensity to close incisions of the skin S and/or to extrude the connection port 810 by epidermal cell proliferation.

The fibrous and/or porous layer 815 can be constructed from any suitable material. In some embodiments, for example, the fibrous and/or porous layer 815 can include one or more biocompatible metallic materials, such as titanium, matte titanium, Nitinol, silver, or stainless steel. In other embodiments, the fibrous and/or porous layer 815 can include one or more polymeric materials, such as, for example, Dacron™, Teflon™, polyolefins, nylon, silicone, flexible polyurethane, polypropylene, vitreous carbon fabric, polytetrafluoroethylene. In yet other embodiments, the fibrous and/or porous layer 815 can include a coating of fine trabecularized carbon and titanium. In yet other embodiments, the fibrous and/or porous layer 815 can include an antimicrobial agent. Such agents can be coated on, implanted within and/or impregnated within the fibrous and/or porous layer 815, the stud 816 and/or the anchor 820. Such agents can include, for example, antibiotics, antifungal, antiviral agents, anti-inflammatory agents, and other healing agents (e.g., silver or silver coatings).

Although connection port 110 shown and described above includes an anchor 120 that extends radially from the stud 116, in some embodiments, the anchor 120 can have any suitable shape and/or orientation relative to the stud 116. For example, in some embodiments, a connection port can include an anchor having an oval shape devoid of sharp edges and/or tight concave surfaces. In other embodiments, a connection port can include an anchor having multiple surfaces configured to maintain a location of the connection port within the body. Such surfaces can be, for example, discontinuous surfaces that are each configured to engage and/or contact a portion of the skin and/or subcutaneous tissue to maintain the location of the connection port within the body. In yet other embodiments, a connection port can include an anchor having multiple members configured to cooperatively maintain a location of the connection port within the body.

Figure 11:
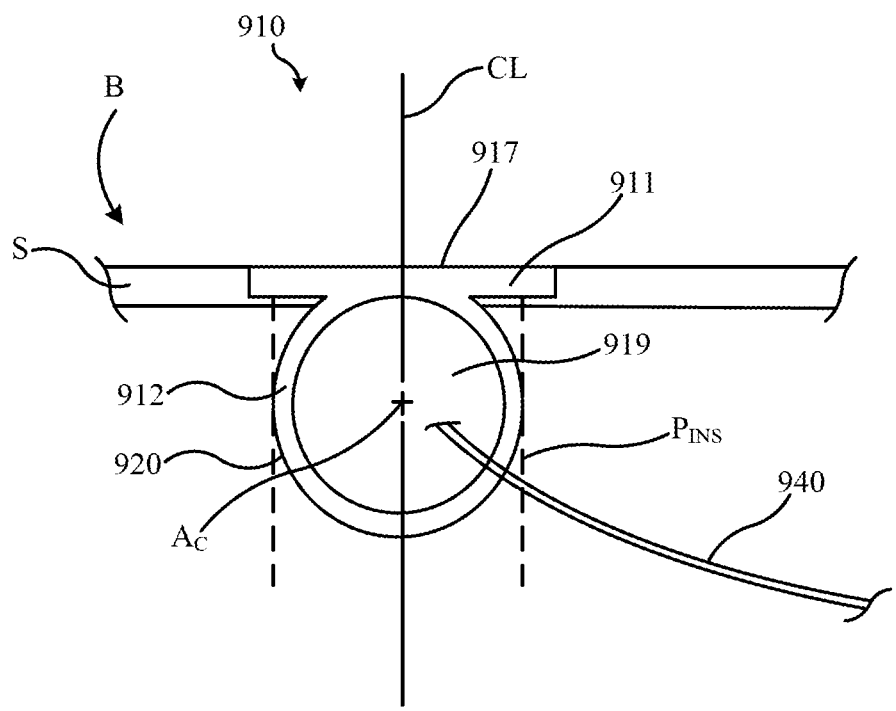
FIG. 11 is a front view of a medical device according to an embodiment of the invention disposed within a body.

FIG. 11 is a front view of a connection port 910 according to an embodiment of the invention disposed percutaneously within a body B. The connection port 910 has a proximal portion 911 and a distal portion 912. The proximal portion 911 includes a connection surface 917. The connection surface 917 is configured to be substantially parallel with an outer surface of the skin S. Said another way, the connection surface 917 is substantially normal to a center line CL of the insertion path $P_{INS}$ through which the connection port 910 is percutaneously inserted into the body B.

The distal portion 912 includes an anchor 920. The anchor 920 has a circular shape about an axis $A_C$ substantially parallel with the outer surface of the skin S. Said another way, the anchor 920 has a circular shape about an axis substantially normal to the center line $C_L$ of the insertion path $P_{INS}$. In some embodiments, for example, the anchor has a toroidal shape about the axis $A_C$. Because FIG. 11 is a front view of the connection port 910, the axis $A_C$ is shown as a point and would extend from the page. The anchor 920 defines an opening 919, a portion of which is disposed beneath the skin S. In this manner, as shown in FIG. 11, the anchor 920 can be disposed about an electrical member 940. As described above, the electrical member 940 can be any implantable member that defines an electrically conductive path for conveying an electrical signal from the connection port 910 to a tissue and/or device within the body B.

Figure 12:
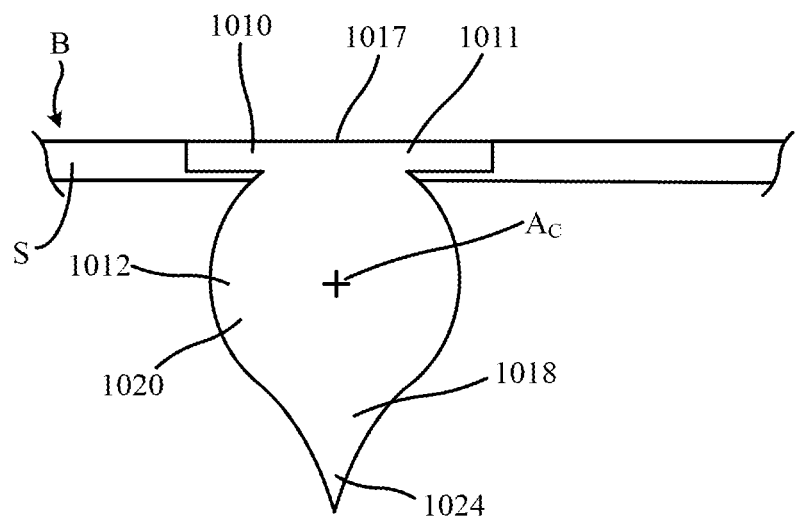
FIG. 12 is a front view of a medical device according to an embodiment of the invention disposed within a body.

FIG. 12 is a front view of a connection port 1010 according to an embodiment of the invention disposed percutaneously within a body B. The connection port 1010 has a proximal portion 1011 and a distal portion 1012. The proximal portion 1011 includes a connection surface 1017. The distal portion 1012 includes an anchor 1020 and a dilator 1018. The anchor 1020 is similar to the anchor 920 described above with reference to FIG. 11 and has a circular shape about an axis $A_C$ substantially parallel with the outer surface of the skin S. The dilator 1018 has a tapered portion 1024 configured to displace a bodily tissue when the connection port 1010 is inserted into the body.

Figure 13:
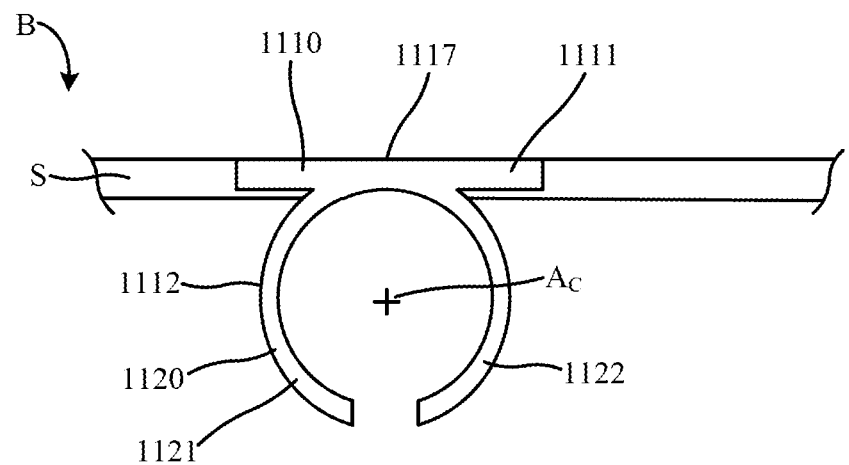
FIG. 13 is a front view of a medical device according to an embodiment of the invention disposed within a body.

Although the connection ports 910 and 1010 shown and described above include an anchor having a continuously circular shape, in other embodiments, a connection port can include an anchor having multiple members that define a discontinuous circular shape. For example, FIG. 13 is a front view of a connection port 1110 according to an embodiment of the invention disposed percutaneously within a body B. The connection port 1110 has a proximal portion 1111 and a distal portion 1112. The proximal portion 1111 includes a connection surface 1117. The distal portion 1112 includes an anchor 1120 having a first member 1121 and a second member 1122. The first member 1121 and the second member 1122 cooperatively define a circular shape about an axis $A_C$ substantially parallel with the outer surface of the skin S. The distal ends of the first member 1121 and the second member 1122 are spaced apart, however, such that the circular shape is discontinuous.

Although the anchors are shown and described above as being in a fixed position relative to other portions of the connection port, in some embodiments, at least a portion of an anchor can move relative to another portion of the connection port. For example, in some embodiments, a connection port can include an anchor having a first member and a second member that is movable relative the first member. In this manner, the second member can move relative to the first member to move the anchor between a first configuration (e.g., an insertion configuration) and a second configuration (e.g., an anchoring configuration). In other embodiments, a connection port can include a monolithically constructed anchor that is movable relative to the proximal end of the connection port. In this manner, the connection port can move between a first configuration and a second configuration. In yet other embodiments, a connection port can include a movable anchor and a biasing member configured to bias the movable anchor in a predetermined configuration (e.g., an insertion configuration or an anchoring configuration).

Figure 14:
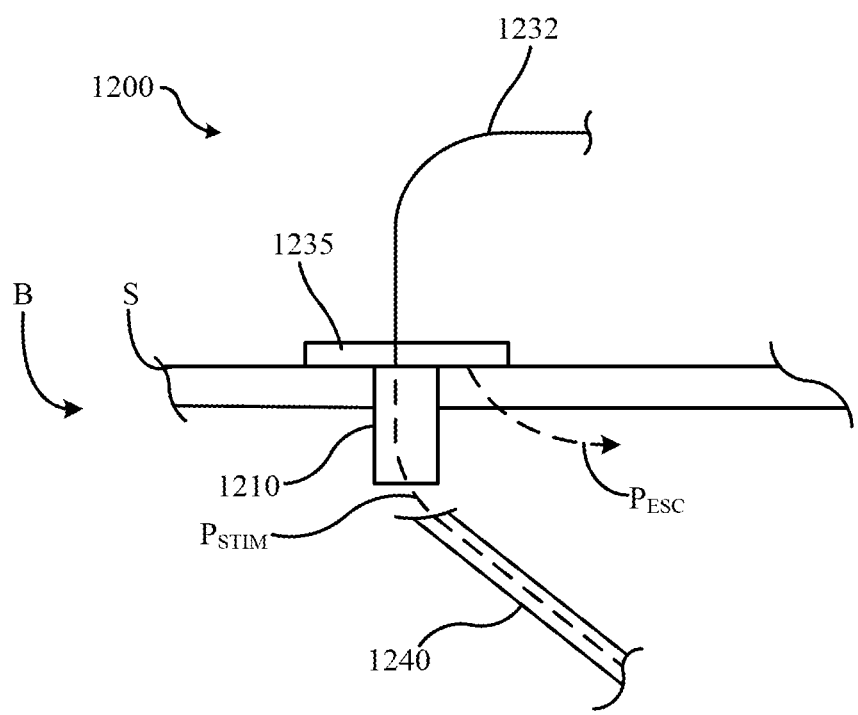
FIG. 14 is a schematic illustration of a portion of a stimulation system according to an embodiment of the invention disposed within a body.

Although the connection wires are shown and described above as being mechanically coupled to a proximal portion of a connection port, in some embodiments, an intervening structure can be used to mechanically and/or electrically couple the connection wires and the connection port. For example, FIG. 14 shows a portion of a stimulation system 1200 according to an embodiment of the invention. The stimulation system 1200 includes at least one connection port 1210, a surface electrode 1235, a connection wire 1232, and an electrical member 1240 implanted within the body B. The connection port 1210, which is similar to the connection ports shown and described above, includes a proximal portion 1211 and a distal portion 1212. As described above, the connection port 1210 defines a conductive path therethrough having an electrical impedance less than an electrical impedance of the skin S.

The connection wire 1232 is mechanically and electrically coupled to the proximal portion 1211 of the connection port 1210 by the surface electrode 1235, which can be, for example, a conductive electrolyte gel electrode. Accordingly, an electrical signal can be conveyed between an area outside of the body and the electrical member 1240 via a stimulation path $P_{STIM}$ that includes the connection wire 1232, the surface electrode 1235, the connection port 1210 and a portion of the subcutaneous tissue. Because a portion of the surface electrode 1235 is in contact with the skin S, some amount of the electrical signal (e.g., the escape current) may be conveyed by the surface electrode 1235 into the body B via an escape path $P_{ESC}$ that includes the skin S. However, because the conductive path defined by the connection port 1210 has an electrical impedance less than an electrical impedance of the skin S, the magnitude of the electrical signal conveyed via the escape path is minimal.

In some embodiments, a connection wire can be mechanically and/or electrically coupled to the connection port via a connector that does not directly contact the skin S. In this manner, the escape current can be further minimized and/or eliminated. In some embodiments, a connector can be a removable connector, such as, for example, a snap connector, an alligator clip, a screw connector, a slide connector or the like. In other embodiments a connector can be non-removable, such as, for example, a soldered connector, a welded connector, a crimped connector or the like.

Figure 15:
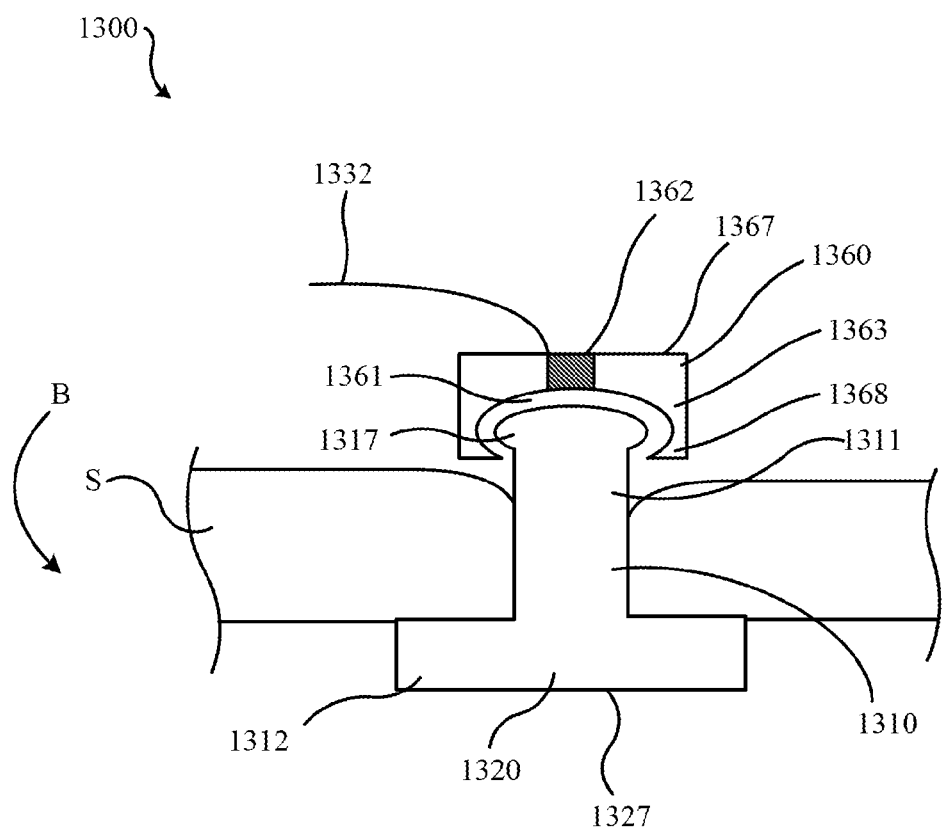
FIG. 15 is a schematic illustration of a portion of a stimulation system according to an embodiment of the invention disposed within a body.

For example, FIG. 15 shows a portion of a stimulation system 1300 according to an embodiment of the invention. The stimulation system 1300 includes at least one connection port 1310, a connector 1360, and a connection wire 1332. The connection port 1310 includes a proximal portion 1311 and a distal portion 1312. The proximal portion 1311 includes a protrusion 1317. The distal portion 1312 includes a terminal surface 1327 and an anchor 1320. As described above, the anchor 1320 is disposed beneath the skin S of the body B to anchor the connection port 1310 in a subcutaneous location within the body B.

The connector 1360 has a proximal end 1367 and a distal end 1368, and includes an outer portion 1363 constructed from a first material having a first electrical conductivity, and an inner portion 1362 constructed from a second material having a second electrical conductivity greater than that of the first material. In this manner, the inner portion 1362 defines an electrically conductive pathway through the connector between the proximal end 1367 and the distal end 1368. In some embodiments, however, the connector 1360 can be constructed from a single material.

The connection wire 1332 is coupled to the proximal end 1367 of the connector 1360. The distal end 1368 of the connector 1360 defines an opening 1361 configured to matingly receive the protrusion 1317 of the connection port 1310. In this manner, the connector 1360 can be removably coupled (e.g., snapped) to the connection port 1310 in a predetermined position relative to the connection port 1310.

Figure 16:
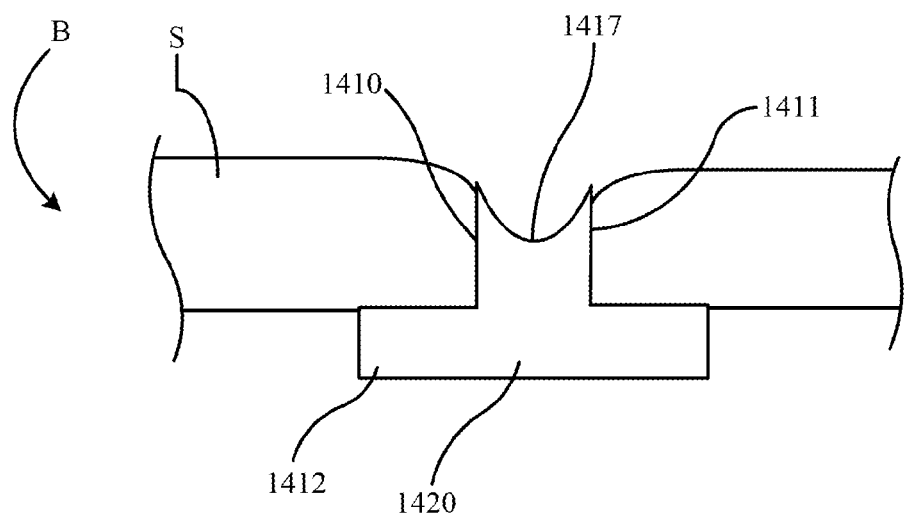
FIG. 16 is a front view of a medical device according to an embodiment of the invention disposed within a body.

Although the connection port 1310 is shown as having a protrusion 1317 that extends above the surface of the skin S and has a convex shape, in other embodiments, a connection port can include any suitable terminal surface that is accessible from a region outside of the body. For example, FIG. 16 shows a connection port 1410 according to an embodiment of the invention. The connection port 1410 includes a proximal portion 1411 and a distal portion 1412. The proximal portion 1411 includes a terminal surface 1417 having a concave shape such that at least a portion of the terminal surface 1417 is disposed below the outer surface of the skin S. The terminal surface 1417 is accessible from a region outside of the body B. As described above, distal portion 1412 includes an anchor 1420 disposed beneath the skin S of the body B to anchor the connection port 1410 in a subcutaneous location within the body B.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope of the invention should not be limited by any of the above-described embodiments. While the invention has been particularly shown and described with reference to specific embodiments thereof, it will be understood that various changes in form and details may be made.

For example, although the stimulation systems shown and described above include an electrical member disposed entirely within the body (e.g., a passive electrical conductor, an electrical device or the like), in some embodiments, a stimulation system can be devoid of an electrical member disposed entirely within the body. For example, in some embodiments, a stimulation system can include an electrical stimulator and a connection port of the types shown and described above. In such stimulation systems, an electrical current can be conveyed from the electrical stimulator to a target tissue via a stimulation path that excludes the skin and includes subcutaneous body tissue.

Although the connection ports are shown and described above as having a terminal surface that is configured to be flush with or above an outer surface of the skin, in some embodiments a connection port can have a terminal surface that is configured to be below an outer surface of the skin (i.e., recessed) while remaining accessible from an area outside of the body. In yet other embodiments, a connection port can have a non-planar terminal surface such that a portion of the terminal surface is disposed above an outer surface of the skin and a portion of the terminal surface is disposed below and outer surface of the skin.

Although various embodiments have been described as having particular features and/or combinations of components, other embodiments are possible having a combination of any features and/or components from any of embodiments where appropriate. For example, in some embodiments, a stimulation system can include any connection port of the types shown and described above and/or any arrangement of external electrical devices, internal electrical devices and/or electrical members as shown and described herein. For example, in some embodiments, a stimulation system can include one or more connection ports having a circular shaped anchor (as discussed above with reference to FIGS. 11-13) and an electrical member in contact with a distal portion of the connection port.

What is claimed is:

1. A system, comprising:
    an electrical device configured to be disposed outside of a body, the electrical device configured to at least produce or receive an electrical signal;
    a passive electrical conductor configured to be disposed entirely within the body, a distal end of the passive electrical conductor including a plurality of electrodes configured to be disposed adjacent a target tissue within the body; and
    a connection port configured to convey the electrical signal between the electrical device and the electrical member, the connection port configured to be percutaneously inserted into the body such that a proximal portion of the connection port is disposed outside of the body and a distal portion of the connection port is disposed within the body, the connection port including a plurality of distinct electrical pathways, each electrical pathway from the plurality of electrical pathways configured to be in electrical communication with a corresponding electrode from the plurality of electrodes,
    the proximal portion of the connection port configured to be operatively coupled to the electrical device, the distal portion of the connection port configured to be spaced apart from the electrical member, the distal end portion of the connection port is operatively coupled to the electrical member by at least one of a galvanic coupling, a capacitive coupling or an inductive coupling.

2. The system of claim 1, wherein the electrical device is at least one of an electrical stimulator or a electrical signal processor.

3. The system of claim 1, wherein:
    the electrical member is a passive electrical conductor, a distal end of the passive electrical conductor including a plurality of electrodes configured to be disposed adjacent a target tissue within the body; and
    the connection port includes a plurality of distinct electrical pathways, each electrical pathway from the plurality of electrical pathways configured to be in electrical communication with a corresponding electrode from the plurality of electrodes.

4. The system of claim 1, wherein the electrical member is any one of a sensor, an amplifier, a power supply, a high voltage generator, a current generator, a switch, a battery charging circuit, an electronic filter, or a processor.

5. The system of claim 4, wherein the connection port includes an electrical conductor having an impedance less than an impedance of a skin.

6. The system of claim 4, wherein:
the stimulator is configured to produce a bi-polar electrical stimulation signal; and
the connection port includes a plurality of distinct electrical pathways configured to convey the bi-polar stimulation signal to the passive electrical member.

7. The system of claim 4, wherein:
the proximal end of the connection port is configured to extend above a surface of a skin; and
the distal end of the connection port includes an anchor configured to be disposed subcutaneously within the body and to limit movement of the connection port within the body.

8. The system of claim 4, further comprising:
a surface electrode configured to be coupled to a surface of a skin of the body, the surface electrode configured to be coupled to the stimulator.

9. A system, comprising:
a stimulator configured to produce an electrical stimulation signal;
an implant configured to be disposed within the body, the implant having a first terminal portion, a second terminal portion and a conductor therebetween, the second terminal portion configured to convey the electrical stimulation signal to a target tissue; and
a connection port configured to be disposed at least partially within the body such that a proximal portion of the connection port is accessible from a region outside of the body and a distal portion of the connection port is disposed within the body, the connection port including an outer portion configured to contact a skin, the outer portion constructed from a material configured to promote bonding of the skin to the outer portion,
the proximal portion of the connection port configured to be coupled to the stimulator, the distal portion of the connection port configured to be electrically coupled to and spaced apart from the first terminal portion of the implant.

10. The system of claim 9, wherein:
the electrical stimulation signal is a first electrical stimulation signal from a plurality of electrical stimulation signals produced by the stimulator;
the second terminal portion of the implant includes a plurality of electrodes, each electrode from the plurality of electrodes configured to convey an electrical stimulation signal from the plurality of electrical stimulation signals to a portion of the target tissue; and
the connection port includes a plurality of distinct electrical pathways configured to convey each electrical stimulation signal from the plurality of electrical stimulation signals to the implant.

11. The system of claim 9, wherein:
the proximal end of the connection port is configured to extend above a surface of a skin; and
the distal end of the connection port includes an anchor configured to be disposed subcutaneously within the body and to limit movement of the connection port within the body.

12. The system of claim 9, wherein the second terminal portion of the implant includes an electrode configured to at least partially engage the target tissue.

13. The system of claim 11, further comprising:
a surface electrode configured to be coupled to a surface of a skin of the body, the surface electrode configured to be coupled to the stimulator.

14. A system, comprising:
an electrical device configured to be disposed outside of a body, the electrical device configured to at least produce or receive an electrical signal;
a passive electrical conductor configured to be disposed entirely within the body, a distal end of the passive electrical conductor including a plurality of electrodes configured to be disposed adjacent a target tissue within the body; and
a connection port configured to convey the electrical signal between the electrical device and the passive electrical conductor, the connection port configured to be percutaneously inserted into the body such that a proximal portion of the connection port is disposed outside of the body and a distal portion of the connection port is disposed within the body, the connection port including a plurality of distinct electrical pathways,
the proximal portion of the connection port configured to be operatively coupled to the electrical device, the distal portion of the connection port configured to be operatively coupled to and spaced apart from the passive electrical conductor such that each electrical pathway from the plurality of electrical pathways is in electrical communication with a corresponding electrode from the plurality of electrodes.

15. A system, comprising:
a stimulator disposed outside of a body, the stimulator configured to produce a bi-polar electrical stimulation signal;
an electrical member configured to be disposed within the body; and
a connection port including a plurality of distinct electrical pathways through which the bi-polar electrical signal can be conveyed between the stimulator and the electrical member, the connection port configured to be percutaneously disposed into the body such that a proximal portion of the connection port is accessible from a region outside of the body and a distal portion of the connection port is disposed within the body,
the proximal portion of the connection port configured to be coupled to the stimulator, the distal portion of the connection port configured to be electrically coupled to and spaced apart from the electrical member.

* * * * *

UNITED STATES PATENT AND TRADEMARK OFFICE
CERTIFICATE OF CORRECTION

PATENT NO. : 8,483,820 B2
APPLICATION NO. : 11/867454
DATED : July 9, 2013
INVENTOR(S) : Yitzhak Zilberman Page 1 of 1

It is certified that error appears in the above-identified patent and that said Letters Patent is hereby corrected as shown below:

In the Claims:

Column 20, line 51, replace Claim 3 with the following: --3. The system of claim 1, wherein the distal end portion of the connection port includes an anchor configured to limit movement of the connection port within the body and a porous coating disposed about at least a portion of the anchor.--.

Column 20, line 61, replace Claim 4 with the following: --4. A system, comprising:
a stimulator disposed outside of a body, the stimulator configured to produce and convey an electrical signal;
a passive electrical member configured to be disposed within the body, the passive electrical member having a first terminal portion, a second terminal portion and a conductor therebetween, the second terminal portion configured to be disposed adjacent a target tissue; and
a connection port configured to convey the electrical signal between the stimulator and the passive electrical member, the connection port configured to be percutaneously disposed into the body such that a proximal portion of the connection port is accessible from a region outside of the body and a distal portion of the connection port is disposed within the body,
the proximal portion of the connection port configured to be coupled to the stimulator, the distal portion of the connection port configured to be electrically coupled to and spaced apart from the passive electrical member, the first terminal portion of the passive electrical member configured to receive the electrical signal from the distal portion of the connection port such that the electrical signal is conveyed to the target tissue via the conductor and the second terminal portion,
the connection port including an outer portion configured to contact a skin, the outer portion constructed from a material configured to promote bonding of the skin to the outer portion.--.

Column 22, line 8, replace "13. The system of claim 11," with --13. The system of claim 9,--.

Signed and Sealed this
Tenth Day of December, 2013

Margaret A. Focarino
*Commissioner for Patents of the United States Patent and Trademark Office*